US009213001B2

(12) United States Patent
Nagahama et al.

(10) Patent No.: US 9,213,001 B2
(45) Date of Patent: Dec. 15, 2015

(54) FOCAL POSITION ADJUSTMENT METHOD AND INSPECTION METHOD

(71) Applicant: NuFlare Technology, Inc., Yokohama (JP)

(72) Inventors: Hiroyuki Nagahama, Saitama (JP); Riki Ogawa, Kanagawa (JP)

(73) Assignee: NuFlare Technology, Inc., Yokohama (JP)

( * ) Notice: Subject to any disclaimer, the term of this patent is extended or adjusted under 35 U.S.C. 154(b) by 0 days.

(21) Appl. No.: 14/566,002

(22) Filed: Dec. 10, 2014

(65) Prior Publication Data

US 2015/0204796 A1    Jul. 23, 2015

(30) Foreign Application Priority Data

Jan. 23, 2014    (JP) .................. 2014-010839

(51) Int. Cl.
| | | |
|---|---|---|
| *G01N 21/00* | (2006.01) | |
| *G01N 21/88* | (2006.01) | |
| *G01N 21/93* | (2006.01) | |
| *G01N 21/956* | (2006.01) | |

(52) U.S. Cl.
CPC ............ *G01N 21/8806* (2013.01); *G01N 21/93* (2013.01); *G01N 21/956* (2013.01); *G01N 2201/06113* (2013.01)

(58) Field of Classification Search
CPC .............. G01N 21/94; G01N 21/956; G01N 21/95607; G01N 2201/06113; G02B 21/0032; G02B 21/247; G03F 9/7026
USPC .............. 356/237.1–237.5; 250/201.2, 201.3, 250/201.4
See application file for complete search history.

(56) References Cited

U.S. PATENT DOCUMENTS

| | | | |
|---|---|---|---|
| 5,572,011 A | 11/1996 | Goto | |
| 8,970,826 B2 * | 3/2015 | Liu | ............... G02B 7/36 356/4.01 |
| 2007/0164194 A1 * | 7/2007 | Kurata | ............... G02B 21/247 250/201.4 |
| 2010/0247085 A1 | 9/2010 | Shiratsuchi et al. | |
| 2011/0315851 A1 * | 12/2011 | Kishima | ............... G02B 21/245 250/201.3 |
| 2014/0111636 A1 * | 4/2014 | Inoue | ............... G01N 21/95607 348/92 |

FOREIGN PATENT DOCUMENTS

| | | |
|---|---|---|
| JP | 7-199052 | 8/1995 |
| JP | 2007-148084 | 6/2007 |
| JP | 2010-230405 | 10/2010 |
| JP | 2014-85217 | 5/2014 |

* cited by examiner

*Primary Examiner* — Hoa Pham
(74) *Attorney, Agent, or Firm* — Oblon, McClelland, Maier & Neustadt, L.L.P.

(57) ABSTRACT

In a focal position adjusting method for an inspection apparatus, the inspection apparatus includes an illumination optical system and an imaging optical system configured to perform a defect inspection of a pattern formed in a sample using an image imaged on a first sensor. The focal position adjusting method includes illuminating the light from the first light source on the sample after transmitting the light through a first slit disposed in the illumination optical system. The light from the first light source is condensed into a second sensor disposed in the imaging optical system. A light intensity distribution of a pupil of the illumination optical system is observed. The focal position of the illumination optical system is adjusted by obtaining each light quantity of the front focus and the rear focus of the image of the first slit projected on the sample based on the light intensity distribution.

10 Claims, 8 Drawing Sheets

FOCAL POSITION ADJUSTMENT METHOD AND INSPECTION METHOD

CROSS-REFERENCE TO THE RELATED APPLICATION

The entire disclosure of the Japanese Patent Application No. 2014-10839, filed on Jan. 23, 2014 including specification, claims, drawings, and summary, on which the Convention priority of the present application is based, are incorporated herein in its entirety.

FIELD OF THE INVENTION

The present invention relates to a Focal Position Adjustment Method and Inspection Method.

A semiconductor device such as a Large Scale Integration (LSI) uses an original image pattern (that is, a mask or a reticle, hereinafter collectively referred to as a mask), a reduced-projection exposure apparatus called a stepper or a scanner exposes and transfers the pattern, thereby producing the semiconductor device.

It is necessary to improve a production yield for costly LSI production. With high integration and large capacity of a Large Scale Integration (LSI), a circuit dimension required for a semiconductor element becomes increasingly narrow. On the other hand, there is a demand for pattern formation having a line width of tens of nanometers in a contemporary typical logic device. The finer the dimensions of an LSI pattern formed on the wafer becomes, the finer the defect of the mask pattern becomes. As fluctuations of various process conditions are absorbed by enhancing dimensional accuracy of the mask, it is necessary to detect the defect of the extremely small pattern in a mask inspection. Therefore, high accuracy is required for an apparatus that inspects the pattern of a mask.

In the inspection apparatus, light output from the light source is emitted onto the mask through an optical system. The mask is mounted on the stage, and the emitted light scans the mask while the stage moves. The light is reflected with respect to the mask, and passes through the lens to form an optical image on a sensor, which serves as a light receiving unit. Then, the mask is inspected based on the optical image captured by the sensor.

In the inspection process, a first slit disposed in an illumination optical system mask pattern surface being an inspection target, and a sensor surface performing a pattern defect inspection all perform an inspection in a conjugate relation, that is, in a state in which a focus is matched. Therefore, it is important to adjust a focus by accurately detecting a focal position of light irradiated on a mask. Here, as a focal position adjusting method, there is a confocal detection method (see Japanese Laid Open Patent Application Publication No. 2007-148084). In the case of this method, light from a light source is transmitted through the first slit disposed in the illumination optical system and is then imaged on the inspection target by an objective lens. Light reflected by the inspection target is incident on a sensor by an imaging optical system. Specifically, after the light is transmitted through the objective lens and is transmitted through a second slit disposed at a position optically conjugate with the first slit, the light is received by the sensor and the output corresponding to an amount of the received light is measured. When an image is in focus at the position of the slit, light quantity becomes maximum and thus the output of the sensor becomes maximum. On the other hand, if the focus deviates from the position of the slit, a part of the light quantity is blocked by the slit and thus the output of the sensor is lowered. Therefore, the deviation amount of the inspection target from the in-focus position can be known by measuring the output of the sensor.

Incidentally, if a slit-shaped light beam is irradiated on the surface of the inspection target on which a fine line pattern is formed, diffracted light is generated in a direction different from regularly reflected light. As a result, both of the regularly reflected light and the diffracted light are included in the light that is transmitted through the second slit disposed in the imaging optical system. At this time, the intensity distribution of the light transmitted through the second slit greatly changes near a boundary between a location where the diffracted light is transmitted through the slit and a location where the diffracted light is blocked by the slit. Since the intensity distribution is greatly changed if the focal position slightly deviates from the in-focus position, the degree of blurring of a slit image formed on a light receiving surface of the sensor is also greatly changed. Therefore, it is difficult to perform high-accuracy adjustment such that the pattern surface of the inspection target is matched with the focal position of the objective lens.

The above-mentioned problem depends on the dimension of the pattern formed on the surface of the inspection target. FIGS. 1 to 3 are plan views of a second slit when viewed from a direction parallel to an optical axis. In these drawings, a solid line represents $0^{th}$ order light at a pupil position, a dashed line represents $+1^{st}$ order diffracted light, and a dashed-dotted line represents $-1^{st}$ order diffracted light.

For example, when the numerical aperture NA of the objective lens is 0.75, the wavelength of the light from the light source is 200 nm, and the opening diameter of the slit is half of the light beam diameter, that is, half of the pupil diameter and the pattern formed in the inspection target is L/S (Line and Space) of 1 µm pitch, as illustrated in FIG. 1, most (more than half) of $+1^{st}$ order diffracted light and $-1^{st}$ order diffracted light are superimposed with $0^{th}$ order light. Therefore, the amount of the diffracted light transmitted through the slit is not greatly changed even when the focal position is changed. Further, for example, when the pattern formed in the inspection target is smaller than 100 nm L/S, as illustrated in FIG. 2, $+1^{st}$ order diffracted light and $-1^{st}$ order diffracted light is not transmitted through the slit. Therefore, the influence of the diffracted light by the change in the focal position may not be considered. However, for example, when pitch of the L/S pattern is 100 nm to 133 nm, as illustrated in FIG. 3, most (more than half) of the $+1^{st}$ order diffracted light and the $-1^{st}$ order diffracted light are transmitted through the slit without being superimposed with the $0^{th}$ order light. In this case, since the amount of the diffracted light transmitted through the slit is changed according to the focal position, the above-described problem occurs.

Recently, as a technique for forming a fine pattern, nanoimprint lithography (NIL) has attracted attention. In this technique, a template having a nanoscale microstructure is pressured on a specific resist formed on a wafer to transfer the fine circuit of the template pattern on the resist. In the nanoimprint technology, to increase productivity, a plurality of duplicate patterns (daughter patterns) is produced using a master pattern as an original plate, and the daughter patterns are used by being mounted on different nanoimprint apparatuses. The daughter pattern is required to be produced accurately corresponding to the master pattern. In the inspection process, high-accuracy inspection is required for both the master template pattern and the daughter pattern. In such patterns, since pitch of some L/S patterns is 100 nm or less and pitch of some patterns is 100 nm to 133 nm L/S, there is a need to accurately adjust a focal position with respect to a sample surface having a wide dimension range of patterns.

The present invention has been made in view of the above problem. In other words, an object of the present invention is to provide a Focal Position Adjusting Method capable of preventing a reduction in focal position adjustment accuracy due to diffracted light.

Furthermore, another object of the present invention is to provide an inspection method capable of preventing a reduction in focal position adjustment accuracy due to diffracted light and thus performing an accurate inspection.

Other challenges and advantages of the present invention are apparent from the following description.

SUMMARY OF THE INVENTION

According to one aspect of the present invention, in a focal position adjusting method for an inspection apparatus, the inspection apparatus includes an illumination optical system that illuminates at least one of light from a first light source and light from a second light source with a longer wavelength than the light from the first light source on a sample through an objective lens, and an imaging optical system that images light reflected by the sample on a first sensor through the objective lens, and performs a defect inspection of a pattern formed in the sample using the image imaged on the first sensor. The focal position adjusting method includes illuminating the light from the first light source on the sample through the objective lens after transmitting the light from the first light source through a first slit disposed in the illumination optical system. The light from the first light source, which is reflected by the sample and transmitted through the objective lens is condensed into a second sensor disposed in the imaging optical system, and is observed a light intensity distribution of a pupil of the illumination optical system. The focal position adjusting method includes illuminating the light from the first light source on the sample through the objective lens after transmitting the light from the first light source through a first slit disposed in the illumination optical system. From the light intensity distribution, in a case where most of diffracted light of the light from the first light source, which is reflected by the sample, is superimposed with $0^{th}$ order light, or in a case where it is determined that the diffracted light is not transmitted through two slits disposed in the imaging optical system; the light from the first light source, which is reflected by the sample and transmitted through the objective lens is branched, and is guided to the two slits disposed in the imaging optical system. A focal position of the illumination optical system is adjusted by obtaining each light quantity of a front focus and a rear focus of an image of the first slit projected on the sample by a focal position adjustment sensor configured to detect light transmitted through one slit and another focal position adjustment sensor configured to detect light transmitted through the other slit. From the light intensity distribution, in a case where it is determined that most of the diffracted light of the light from the first light source, which is reflected by the sample, is not superimposed with the $0^{th}$ order light and is transmitted through the two slits disposed in the imaging optical system, the light from the second light source is illuminated on the sample through the objective lens after the light from the second light source is transmitted through the first slit by changing to the light from the first light source. The light reflected by the sample is branched, and is guided to the two slits disposed in the imaging optical system. The focal position of the illumination optical system is adjusted by obtaining each light quantity of the front focus and the rear focus of the image of the first slit projected on the sample by the focal position adjustment sensor configured to detect the light transmitted through one slit and the another focal position adjustment sensor configured to detect light transmitted through the other slit.

In another aspect of the present invention, in a focal position adjusting method of an inspection apparatus, the inspection apparatus includes an illumination optical system that illuminates light from a light source on a sample through an objective lens, and an imaging optical system that images light reflected by the sample on a first sensor through the objective lens, and performs a defect inspection of a pattern formed in the sample using the image imaged on the first sensor. The focal position adjusting method includes illuminating the light from the light source on the sample through the objective lens after transmitting the light from the light source through a first slit. The light from the light source, which is reflected by the sample and transmitted through the objective lens is branched, and is condensed into a second sensor disposed in the imaging optical system. A light intensity distribution of a pupil of the illumination optical system is observed. In a case where it is determined from the light intensity distribution that diffracted light is generated in an X direction, the branched light is further branched into at least two lights. One of the branched lights is guided to a second slit and a third slit, of which a longitudinal direction of an opening is an X direction. The focal position is adjusted by obtaining each light quantity of a front focus and a rear focus of an image of the first slit projected on the sample by a third sensor and a fourth sensor configured to detect light transmitted through the slits, respectively. In a case where it is determined from the light intensity distribution that the diffracted light is generated in a Y direction, the other light of the at least two branched lights is guided to a fourth slit and a fifth slit, of which a longitudinal direction of an opening is a Y direction. The focal position is adjusted by obtaining each light quantity of the front focus and the rear focus of the image of the first slit projected on the sample by a fifth sensor and a sixth sensor configured to detect light transmitted through the slits, respectively.

In another aspect of the present invention, a focal position adjusting method uses an illumination optical system that illuminates at least one of light from a first light source and light from a second light source with a longer wavelength than the light from the first light source on a sample through an objective lens, and an imaging optical system that images light reflected by the sample on a first sensor through the objective lens, and performs a defect inspection of a pattern formed in the sample using the image imaged on the first sensor. The focal position adjusting method includes illuminating the light from the first light source on the sample through the objective lens after transmitting the light from the first light source through a first slit disposed in the illumination optical system. The light from the first light source, which is reflected by the sample and transmitted through the objective lens, is condensed into a second sensor disposed in the imaging optical system. A light intensity distribution of a pupil of the illumination optical system is observed. From the light intensity distribution, in a case where most of diffracted light of the light from the first light source, which is reflected by the sample, is superimposed with $0^{th}$ order light, or in a case where it is determined that the diffracted light is not transmitted through two slits disposed in the imaging optical system; the light from the first light source, which is reflected by the sample and transmitted through the objective lens, is branched, and is guided the light to the two slits disposed in the imaging optical system. A focal position of the illumination optical system is adjusted by obtaining each light quantity of a front focus and a rear focus of an image of the first slit projected on the sample by a focal position adjustment sensor configured to detect light transmitted through one slit and another focal position adjustment sensor configured to detect light transmitted through the other slit. From the light intensity distribution, in a case where it is determined that most of the diffracted light of the light from the first light source, which is reflected by the sample, is not superimposed with the $0^{th}$ order light and is transmitted through the two slits disposed in the imaging optical system, the light from the second light source is illuminated on the sample through the objective lens after the light from the second light source is transmitted through the first slit by changing to the light from the first light source. The light reflected by the sample is branched, and is guided to the two slits disposed in the imaging optical system. The focal position of the illumination optical system is adjusted by obtaining each light quantity of the front focus and the rear focus of the image of the first slit projected on the sample by the focal position adjustment sensor configured to detect the light transmitted through one slit and the another focal position adjustment sensor configured to detect light transmitted through the other slit. The position of the sample is adjusted such that the focal position is focused on the pattern surface of the sample. Light reflected by the sample is imaged on the first sensor through the objective lens. The defect inspection of the pattern of the sample is performed using the image.

In another aspect of the present invention, a focal position adjusting method uses an illumination optical system that illuminates light from a light source on a sample through an objective lens, and an imaging optical system that images light reflected by the sample on a first sensor through the objective lens, and performs a defect inspection of a pattern formed in the sample using the image imaged on the first sensor. The focal position adjusting method includes illuminating the light from the light source on the sample through the objective lens after transmitting the light from the light source through a first slit. The light from the light source, which is reflected by the sample and transmitted through the objective lens is branched, is condensed into a second sensor disposed in the imaging optical system. A light intensity distribution of a pupil of the illumination optical system is observed. In a case where it is determined from the light intensity distribution that diffracted light is generated in an X direction, the branched light is further branched into at least two lights. One of the branched lights is guided to a second slit and a third slit, of which a longitudinal direction of an opening is an X direction. The focal position is adjusted by obtaining each light quantity of a front focus and a rear focus of an image of the first slit projected on the sample by a third sensor and a fourth sensor configured to detect light transmitted through the slits, respectively. In a case where it is determined from the light intensity distribution that the diffracted light is generated in a Y direction, the other light of the at least two branched lights is guided to a fourth slit and a fifth slit, of which a longitudinal direction of an opening is a Y direction. The focal position is adjusted by obtaining each light quantity of the front focus and the rear focus of the image of the first slit projected on the sample by a fifth sensor and a sixth sensor configured to detect light transmitted through the slits, respectively. The position of the sample is adjusted such that the focal position is focused on the pattern surface of the sample. Light reflected by the sample is imaged on the first sensor through the objective lens. The defect inspection of the pattern of the sample is performed using the image.

DETAILED DESCRIPTION OF THE EMBODIMENTS

Embodiment 1

The Focal Position Adjustment Method, according to the present embodiment will be described using FIG. 4.

Figure 4:
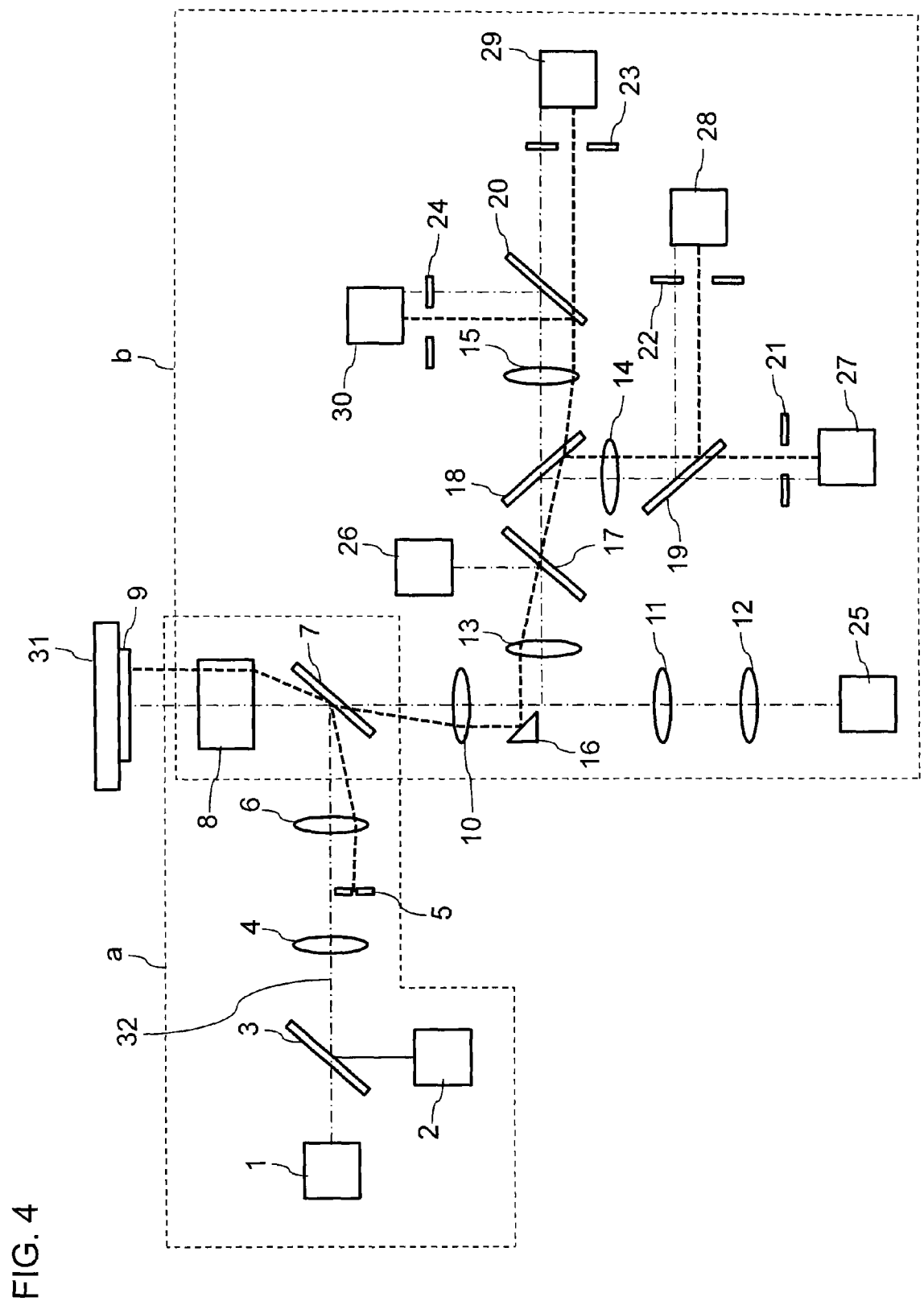
FIG. 4 is an example of a schematic diagram of an optical system used for a focal position adjustment according to the embodiment 1.

FIG. 4 is an example of a schematic diagram of an optical system used for a focal position adjustment. The optical system includes an illumination optical system (a) configured to illuminate a sample 9 in which patterns to be inspected are formed, and an imaging optical system (b) configured to image or condense light reflected by the sample 9 on light receiving surfaces of sensors 25, 26, 27, 28, 29, and 30. Here, the sensor 25 is used to capture an optical image for the defect inspection of the pattern of the sample 9. Furthermore, the sensors 26, 27, 28, 29, and 30 are used to adjust the focal position of the light illuminating the sample 9.

Generally, a plurality of patterns having different dimensions is formed in a sample to be inspected. As described above, the focal position adjustment problem caused by diffracted light depends on the dimension of the pattern. That is, in the patterns having the dimensions as described with reference to FIG. 1 or 2, the influence of the diffracted light may not be considered. However, in the case of the patterns having the dimensions as described in FIG. 3, most (more than half) of the diffracted light is transmitted through the slit without being superimposed with the $0^{th}$ order light. Therefore, when the focal position is changed, the amount of the diffracted light, which means intensity distribution of the light, is drastically is changed, making it difficult to adjust the focal position.

When the opening diameter of the slit and the dimension of the pattern formed in the sample are determined, whether or not the diffracted light is transmitted through the slit depends on the wavelength of the illumination light. Therefore, as in the example of FIG. 3, in a case where the diffracted light influences the focal position adjustment, it is possible to make it unnecessary to consider the influence of the diffracted light in the example of FIG. 1 or 2 by changing the wavelength of the illumination light.

Figure 2:
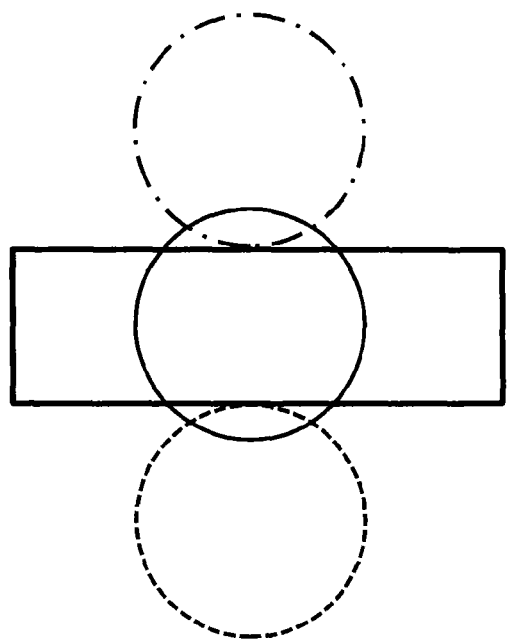
FIG. 2 is another schematic diagram of a position relation between a slit disposed in an imaging optical system, and the regularly reflected light and the diffracted light transmitted through the slit.
Figure 1:
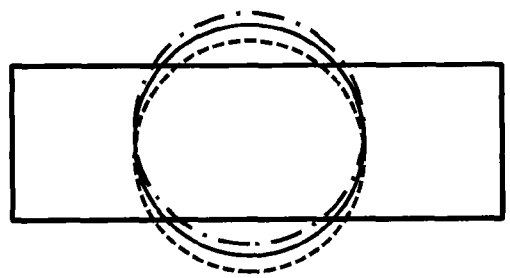
FIG. 1 is a schematic diagram of a position relation between a slit disposed in an imaging optical system, and the regularly reflected light and the diffracted light transmitted through the slit.
Figure 3:
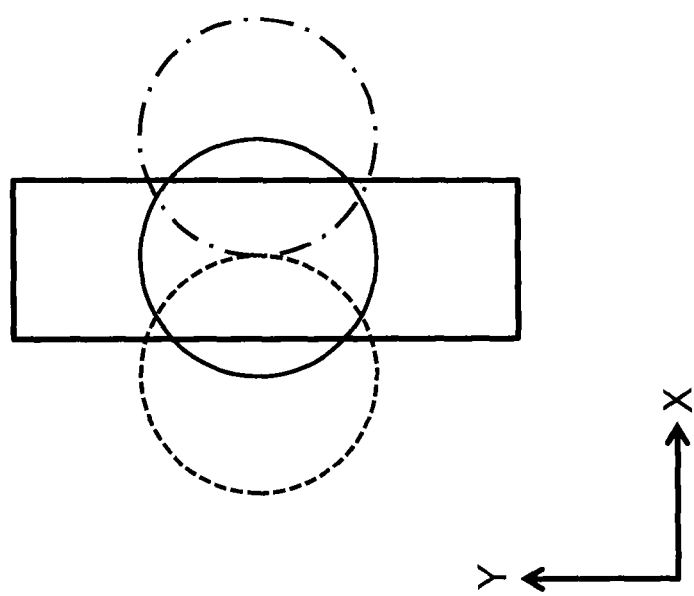
FIG. 3 is another schematic diagram of a position relation between a slit disposed in an imaging optical system, and the regularly reflected light and the diffracted light transmitted through the slit.

In the present embodiment, the sensor 26 of FIG. 4 observes the intensity distribution of the pupil as illustrated in FIGS. 1 to 3. Therefore, a CCD (charge coupled device) image sensor, which is a two-dimensional sensor, is preferably used as the sensor 26.

Here, the L/S pattern of 133 nm is described as an example. An angle θ of a light beam captured by an objective lens is defined using a numerical aperture NA and is expressed as Formula (1).

$$NA = \sin\theta \quad (1)$$

Therefore, for example, when NA=0.75, θ=±48.59 degrees. On the other hand, as in the line-and-space pattern, in the repetitive pattern with directionality, $1^{st}$ order light is diffracted at an angle θ at which the relationship of Formula (2) is established.

$$\sin\theta = \frac{\lambda}{P} \quad (2)$$

λ of Formula (2) represents a wavelength of light from a light source. Furthermore, P is a period of the repetitive pattern and corresponds to twice the value of L/S pitch. In the example of FIG. 3, since the wavelength X, of the light from the light source is 200 nm and L/S pitch is 133 nm, the relationship of Formula (3) is established.

$$\sin\theta = \frac{200}{2 \times 133} = 0.75 \quad (3)$$

The value "0.75" of Formula (3) is matched with the numerical aperture NA of the objective lens. Therefore, $+1^{st}$ order light and $-1^{st}$ order light are shifted to edges of the pupil with respect to $0^{th}$ order light located in the circle as the center of the pupil drawn by the solid line in FIG. 3.

On the other hand, increasing the wavelength λ of the light from the light source is similar to decreasing the period P of the repetitive pattern in Formula (2). Therefore, if the wavelength is increased, as in the example of FIG. 2, $+1^{st}$ order diffracted light and $-1^{st}$ order diffracted light are not transmitted through the slit, and the influence of the diffracted light due to the change in the focal position may not be considered. Furthermore, the resolution of the imaging optical system (b) is proportional to λ/NA. Therefore, when the wavelength λ is increased, the period of the pattern that can be resolved is increased and the resolution is reduced. However, if two light sources with different wavelengths are prepared so as to be selected from two wavelengths, light with a large wavelength λ is used only for a focal position adjustment, and light having a small wavelength λ is used to obtain an optical image for inspection, therefore the reduction of the resolution is not caused and the reduction of the focal position adjustment accuracy due to the diffracted light can be prevented.

In the present embodiment, the optical system of FIG. 4 includes a light source 1 configured to emit light of a wavelength λ1, and a light source 2 configured to emit light of a wavelength λ2. In the present embodiment, the wavelength λ1 can be set to 200 nm and the wavelength λ2 can be set to 266 nm. Here, when the light of the wavelength λ1 illuminates a specific pattern, it is assumed that most (more than half) of diffracted light is transmitted through the slit without being superimposed with $0^{th}$ order light and it is therefore difficult to adjust the focal position. Changing the illumination light to the wavelength λ2 (λ1<λ2) is similar to decreasing the period P of the repetitive pattern in Formula (2). That is, since the diffracted light is not transmitted through the slit, it is possible to improve the focal position adjustment accuracy. The way of setting the wavelength λ2 with respect to the wavelength λ1 is the same as above. That is, the angle θ of the light beam captured by the objective lens is expressed as Formula (1) by using the numerical aperture NA. On the other hand, as in the line-and-space pattern, in the repetitive pattern with directionality, $1^{st}$ order light is diffracted at an angle θ at which the relationship of Formula (2) is established. Therefore, when the wavelength λ1 (λ1=200 nm) of the light from the light source and the pitch of the line-and-space pattern is 133 nm, sin θ is calculated with 0.75 from the relationship of Formula (3) and the value is equal to the numerical aperture NA of the objective lens. Therefore, the $+1^{st}$ order light and the $-1^{st}$ order light are shifted to edges of the pupil with respect to the $0^{th}$ order light located in the center of the pupil. Hence, in theory, when the wavelength is longer than 200 nm, the $+1^{st}$ order light and the $-1^{st}$ order light are not transmitted. However, in practice, the wavelength is set to, for example, λ2=266 nm as in the present embodiment, considering a desired margin.

For example, the light of the wavelength of 200 nm from the light source 1 illuminates the sample 9, and the sensor 26 observes the light intensity distribution of the pupil of the illumination optical system (a) (specifically, it refers to the pupil of the objective lens 8 or the pupil at a position conjugate therewith, the same applies hereinafter). As a result, in a case where the light intensity distribution is given as illustrated in FIG. 1, it is considered that most (more than half) of the $+1^{st}$ order diffracted light and the $-1^{st}$ order diffracted light are superimposed with the $0^{th}$ order light. An amount of diffracted light that is transmitted through the slits 21, 22, 23, and 24 and is incident on the sensors 27, 28, 29, and 30 is not greatly changed even when the focal position is changed. Therefore, after the focal position is detected using the light and the position of the sample 9 is adjusted such that the focal position is focused on the pattern surface of the sample 9, the sensor 25 captures an optical image of the sample 9 and the defect inspection is performed using the acquired optical image.

Furthermore, when the result obtained by observing the light intensity distribution of the pupil of the illumination optical system (a) by the sensor 26 is given as illustrated in FIG. 2, the $+1^{st}$ order diffracted light and the $-1^{st}$ order diffracted light are not transmitted through the slit. Therefore, the influence of the diffracted light due to the change in the focal position may not be considered. Therefore, even in this case, after the focal position is detected using the light from the light source 1 and the position of the sample 9 is adjusted such that the focal position is focused on the pattern surface of the sample 9, the sensor 25 captures the optical image of the sample 9 and the defect inspection is performed using the acquired optical image.

On the other hand, when the result obtained by observing the light intensity distribution of the pupil of the illumination optical system (a) by the sensor 26 is given as illustrated in FIG. 3, most (more than half) of the $+1^{st}$ order diffracted light and the −1$^{st}$ order diffracted light is transmitted through the slits 21, 22, 23, and 24 without being superimposed with the 0$^{th}$ order light. Therefore, an amount of diffracted light that is transmitted through these slits and is incident on the sensors 27, 28, 29, and 30 is changed according to the focal position. In such a case, the light from the light source 2, instead of the light source 1, illuminates the sample 9. The light intensity distribution observed by the sensor 26 is given as illustrated in FIG. 2, and the order diffracted light and the −1$^{st}$ order diffracted light are not transmitted through the slits 21, 22, 23, and 24. Therefore, after the focal position is detected using the light from the light source 2 and the position of the sample 9 is adjusted such that the focal position is focused on the pattern surface of the sample 9, the sensor 25 captures the optical image of the sample 9 and the defect inspection is performed using the acquired optical image.

Next, the focal position adjustment method according to the present embodiment will be described.

As illustrated in FIG. 4, the illumination optical system (a) includes a light source 1 as a first light source and a light source 2 as a second light source, a dichroic mirror 3, lenses 4 and 6, a slit 5 as a first slit, a half mirror 7, and an objective lens 8. On the other hand, the imaging optical system (b) includes an objective lens 8, half mirrors 7, 17, 19, and 20, lenses 10, 11, 12, 13, 14, and 15, a mirror 16, a dichroic mirror 18, a slit 21 as a second slit, a slit 22 as a third slit, a slit 23 as a fourth slit, a slit 24 as a fifth slit, a sensor 25 as a first sensor, a sensor 26 as a second sensor, a sensor 27 as a first focal position adjustment sensor, a sensor 28 as a second focal position adjustment sensor, a sensor 29 as a third focal position adjustment sensor, and a sensor 30 as a fourth focal position adjustment sensor. The optical path of the illumination light and the optical path of the light reflected by the sample 9 are shared from the sample 9 to the half mirror 7. Both of the dichroic mirrors 3 and 18 are a light-separating unit that transmits the light from the light source 1 and reflects the light from the light source 2. Furthermore, there is also a dichroic mirror that reflects the light from the light source 1 and transmits the light from the light source 2. In addition, the light-separating unit is not limited to the dichroic mirror. For example, the light-separating unit may be a color CCD or the like.

The sample 9 is placed on a stage 31 that is movable in an X direction, a Y direction, and a Z direction. The sample 9 is, for example, a mask used to transfer a fine circuit pattern on a wafer or a glass substrate, a master pattern or a daughter pattern used in a nanoimprint lithography technology, or the like, but is not limited thereto. The sample 9 can be a wafer or a glass substrate where a pattern on a mask is transferred.

Each of the light sources 1 and 2 can be a laser light source. In the present embodiment, the wavelength of the light emitted from the light source 1 is set to 200 nm and the wavelength of the light emitted from the light source 2 is set to 266 nm.

The light emitted from the light source 1 propagates along an optical axis 32. The light is transmitted through the dichroic mirror 3 and the lens 4 and illuminates the slit 5. Thereafter, a part of the light is transmitted through the slit 5 and is incident on the lens 6. A width of the slit 5 is as thin as possible in order to approximate a line light source.

The light refracted by the lens 6 is incident on the half mirror 7. The half mirror 7, for example, is disposed to be inclined 45 degrees with respect to the optical axis 32. The half mirror 7 reflects about half of the incident light and transmits the remaining half. Therefore, a part of the light incident on the half mirror 7 from the lens 6 is reflected in a direction of the sample 9. That is, the optical axis 32 is bent 90 degrees by the half mirror 7.

The illumination light reflected by the half mirror 7 is incident on the objective lens 8. The objective lens 8 can be configured such that a plurality of lenses is disposed in a lens barrel. The pupil of the objective lens 8 images an image of the light source 1. The objective lens 8 diffracts the incident light and then illuminates the sample 9. As described above, a part of the illumination light is transmitted through the slit 5. Therefore, the image of the slit 5 is projected on the sample 9. At this time, the image of the slit 5 is projected on a region different from an inspection field of view.

The light reflected by the sample 9 propagates to the half mirror 7 along the optical path shared with the illumination light. That is, the reflected light is refracted by the objective lens 8 and is incident on the half mirror 7. The light refracted by the objective lens 8 is a substantially parallel light beam. A part of the light is transmitted through the half mirror 7 and is incident on the lens 10.

A part of the light transmitted through the lens 10 is reflected by the mirror 16 to bend the optical path and is incident on the lens 13. Here, the reflection by the mirror 16 makes the reflected light of the image of the slit 5 projected on the sample 9. The lens 13 refracts the incident light and makes the refracted light incident on the half mirror 17. The light reflected by the half mirror 17 is incident on the sensor 26. As described above, the sensor 26 is used to observe the light intensity distribution of the pupil of the illumination optical system (a). When the observed light intensity distribution is given as illustrated in FIG. 1 or 2, the influence of the diffracted light due to the change in the focal position is not a problem. Therefore, the focal position is adjusted by the light from the light source 1 as follows.

The light, which is reflected by the mirror 16, incident on the half mirror 17 by the lens 13, and transmitted through the half mirror 17, is transmitted through the dichroic mirror 18 and is incident on the half mirror 20 by the lens 15. Here, the light is branched by the half mirror 20. The light transmitted through the half mirror 20 is further transmitted through the slit 23 and is then incident on the sensor 29. On the other hand, the light reflected by the half mirror 20 is transmitted through the slit 24 and is then incident on the sensor 30. Here, light transmitted through the slits 23 and 24 and incident on the sensors 29 and 30 is reflected light of the image of the slit 5 projected on the sample 9.

The slit 23 is disposed in front of the conjugate position of the sample 9 (front focus), and the slit 24 is disposed in the rear of the conjugate position of the sample 9 (rear focus). Further, the slit 24 may be disposed in front of the conjugate position of the sample 9 (front focus), and the slit 23 may be disposed in the rear of the conjugate position of the sample 9 (rear focus). The width of the slits 23 and 24 is a value corresponding to half the light beam spread by the numerical aperture NA of the objective lens 8, that is, half the pupil diameter of the objective lens 8. In the sensors 29 and 30, for example, a photodiode or a photomultiplier tube is preferably used.

The sensor 29 detects a light quantity of the front focus. On the other hand, the sensor 30 detects a light quantity of the rear focus. When comparing the light quantity of the sensor 29 with the light quantity of the sensor 30 by changing the focal position of the light, a light quantity ratio of the sensor 29 to the sensor 30 is changed according to the shift amount of the focal position. A location where the light quantity ratio is 1:1 is the optimum focal position and has the maximum contrast.

Generally, when the output of the sensor being the front focus is $\alpha$, the output of the sensor being the rear focus is $\beta$, and the output of the sensor without slit is γ, the displacement amount Z from the in-focus position of the object is given by Formula (4).

$$Z = f\left(\frac{\alpha}{\gamma}, \frac{\beta}{\gamma}\right) \quad (4)$$

In Formula (4), γ is the output of the sensor with respect to the total light quantity after the optical path is branched by the half mirror 20, and the normalized light quantities at the respective in-focus positions are (α/γ) and (β/γ). The placement amount Z from the in-focus position of the object is given as the function of the normalized light quantity. The function f can be obtained by geometrically calculating blurring at each focal position with respect to the displacement amount Z and calculating a ratio of passing through the slit. Further, it can be obtained by an experiment using a test sample, a displacement amount of which is already known.

A height of the stage 31 is adjusted based on the displacement amount Z obtained using Formula (4), that is, the displacement amount from the in-focus position of the sample 9.

On the other hand, when the light intensity distribution observed by the sensor 26 is given as illustrated in FIG. 3, the influence of the diffracted light due to the change in the focal position becomes a problem. Therefore, the illumination is changed from the light source 1 to the light source 2.

The light emitted from the light source 2 propagates along an optical axis 32. The light is reflected by the dichroic mirror 3 and is further transmitted through the lens 4. Consequently, the light becomes parallel light. After that, in a similar manner to the light emitted from the light source 1, the light is transmitted through the slit 5, is incident on the lens 6, is reflected by the half mirror 7, and is incident on the objective lens 8. The objective lens 8 refracts the incident light and illuminates the sample 9. Since the illumination light is transmitted through the slit 5, the image of the slit 5 is projected on the sample 9. At this time, in the sample 9, the image of the slit 5 is projected on a region different from the inspection field of view.

The light reflected by the sample 9 propagates to the half mirror 7 along the optical path shared with the illumination light. The light transmitted through the half mirror 7 is transmitted through the lens 10 and is then reflected by the mirror 16, thereby bending the optical path. Here, the reflection by the mirror 16 is performed such that the light becomes the reflected light of the image of the slit 5 projected on the sample 9. Subsequently, the light is transmitted through the lens 13, is further transmitted through the half mirror 17, and is reflected by the dichroic mirror 18, thereby bending the optical path. That is, due to the dichroic mirror 18, the light emitted from the light source 2 propagates along the optical path different from the light emitted from the light source 1.

The light reflected by the dichroic mirror 18 is incident on the half mirror 19 by the lens 14. Here, the light is branched by the half mirror 19. The light transmitted through the half mirror 19 is further transmitted through the slit 21 and is incident on the sensor 27. On the other hand, the light reflected by the half mirror 19 is transmitted through the slit 22 and is then incident on the sensor 28. At this time, the light, which is transmitted through the slits 21 and 22 and is incident on the sensors 27 and 28, is the reflected light of the image of the slit 5 projected on the sample 9.

The slit 21 is disposed in front of the conjugate position of the sample 9 (front focus), and the slit 22 is disposed in the rear of the conjugate position of the sample 9 (rear focus).

Further, the slit 22 may be disposed in front of the conjugate position of the sample 9 (front focus), and the slit 21 may be disposed in the rear of the conjugate position of the sample 9 (rear focus). In the sensors 27 and 28, for example, a photodiode or a photomultiplier tube is preferably used.

The sensor 27 detects a light quantity of the front focus. On the other hand, the sensor 28 detects a light quantity of the rear focus. When comparing the light quantity of the sensor 27 with the light quantity of the sensor 28 by changing the focal position of the light, a light quantity ratio of the sensor 27 to the sensor 28 is changed according to the shift amount of the focal position. A location where the light quantity ratio is 1:1 is the optimum focal position and has the maximum contrast.

As described above, the displacement amount Z from the in-focus position of the object is given by Formula (4).

$$Z = f\left(\frac{\alpha}{\gamma}, \frac{\beta}{\gamma}\right) \quad (4)$$

A height of the stage 31 is adjusted based on the displacement amount Z obtained using Formula (4), that is, the displacement amount from the in-focus position of the sample 9.

As such, in the present embodiment, the light source 1 emitting the light of the wavelength λ1 and the light source 2 emitting the light of the wavelength λ2 are prepared, the light of the wavelength of 200 nm from the light source 1 illuminates the sample 9, and the light intensity distribution of the pupil of the illumination optical system (a) is observed by the sensor 26. As a result, in a case where the influence of the diffracted light due to the change in the focal position is not a problem, the focal position is detected using the light from the light source 1 and the position of the sample 9 is adjusted such that the focal position is focused on the pattern surface of the sample 9. Then, the optical image of the sample 9 is captured by the sensor 25 and the defect inspection is performed using the acquired optical image.

On the other hand, as a result of observing the light intensity distribution of the pupil of the illumination optical system (a) by the sensor 26, in a case where the amount of the diffracted light incident on the sensors 27, 28, 29, and 30 used for the focal position adjustment is changed by the focal position, the light from the light source 2, instead of the light source 1, illuminates the sample 9. Then, after the focal position is detected using the light from the light source 2 and the position of the sample 9 is adjusted such that the focal position is focused on the pattern surface of the sample 9, the optical image of the sample 9 is captured by the sensor 25 and the defect inspection is performed using the acquired optical image.

Further, the optical path of the light imaged on the sensor 25 is as follows. The light, which is emitted from the light source 1 or the light source 2, transmitted through the lenses 4 and 6, and then reflected by the half mirror 7, is illuminated by the objective lens 8 on a region in which the pattern of the sample 9 to be inspected is provided. Furthermore, the illumination light is not superimposed on the sample 9 with the image of the slit 5 projected on the sample 9. After that, the light reflected by the sample 9 propagates to the half mirror 7 along the optical path shared with the illumination light. Then, after the light transmitted through the half mirror 7 is transmitted through the lens 10, the light is further transmitted through the lenses 11 and 12 and is imaged on the sensor 25. Examples of the sensor 25 include a line sensor in which CCD cameras being imaging elements are arranged in a row. In the line sensor, for example, a TDI (time delay integration) sensor can be used.

In the above manner, the reduction in the focal position adjustment accuracy due to the diffracted light can be prevented, making it possible to adjust the focal position.

Further, in the present embodiment, in the imaging optical system (b), the optical path of the light from the light source 1 and the optical path of the light from the light source 2 are separated by the dichroic mirror 18, and the light from the light source 1 is guided to the slits 21 and 22. The respective light quantities of the front focus and the rear focus of the image of the slit 5 projected on the sample 9 are obtained by the sensor 27 detecting the light transmitted through the slit 21 and the sensor 28 detecting the light transmitted through the slit 22. Then, the focal position is adjusted. Further, by guiding the light from the light source 2 to the slits 23 and 24, the focal position is adjusted in a similar manner by the sensor 29 detecting the light transmitted through the slit 23 and the sensor 30 detecting the light transmitted through the slit 24. However, the present invention is not limited thereto. The optical path of the light from the light source 1 and the optical path of the light from the light source 2 may not be branched. In this case, since the sensor for the focal position adjustment and the slit corresponding thereto are shared with the light from the light source 1 and the light from the light source 2, there is an advantage in that the apparatus can be made compact. On the other hand, according to the configuration of the present embodiment, since the optical path is branched by the dichroic mirror 18, two wavelengths can be illuminated at the same time.

Embodiment 2

As described above, when the slit-shaped light beam is irradiated on the surface of the inspection target in which the fine line patterns are formed, the diffracted light is generated in a direction different from the regularly reflected light. As a result, both of the regularly reflected light and the diffracted light are included in the light transmitted through the slit disposed in the imaging optical system. At this time, the intensity distribution of the light transmitted through the second slit is increased near the boundary between a location where the diffracted light is transmitted through the slit and a location where the diffracted light is blocked by the slit. Since the intensity distribution is greatly changed if the focal position slightly deviates from the in-focus position, the degree of blurring of the slit image formed on the light receiving surface of the sensor is also greatly changed. Therefore, it is difficult to highly accurately adjust the relative position of the pattern surface of the inspection target with respect to the focal position of the objective lens.

Incidentally, since many patterns are formed on the surface of the inspection target in two directions perpendicular to each other, the diffracted light is easily generated in the two directions. Therefore, in order not to be influenced by the diffracted light, the direction in which the patterns are formed is not matched with the longitudinal direction of the slit-shaped illumination region.

Figure 5:
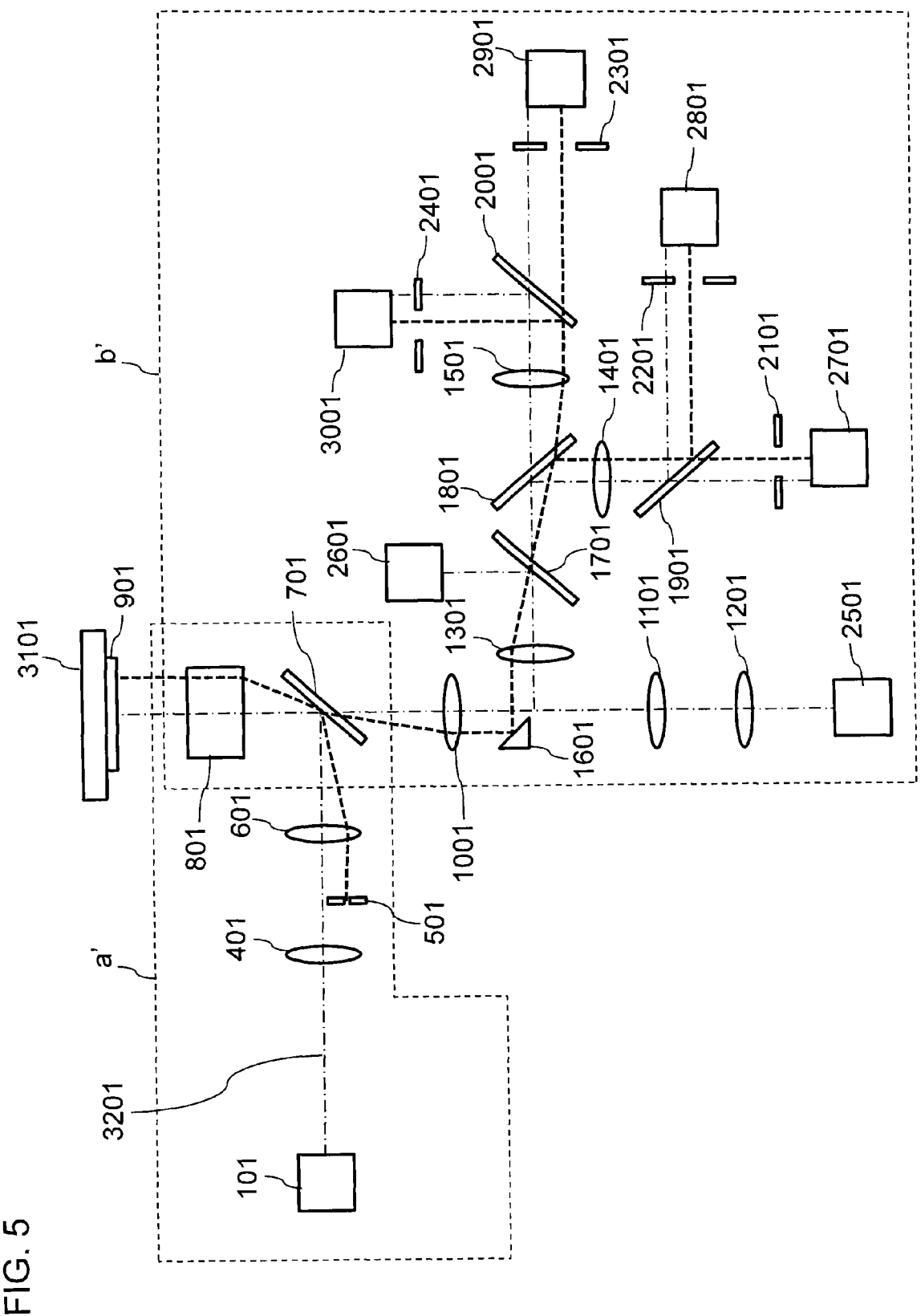
FIG. 5 is an example of a schematic diagram of an optical system used for a focal position adjustment according to the embodiment 2.

FIG. 5 shows an optical system for explaining the focal position adjustment method according to the present embodiment.

As illustrated in FIG. 5, the illumination optical system (a') includes a light source 101, lenses 401 and 601, a slit 501 as a first slit, a half mirror 701, and an objective lens 801. On the other hand, the imaging optical system (b') includes an objective lens 801, half mirrors 701, 1701, 1801, 1901, and 2001, lenses 1001, 1101, 1201, 1301, 1401, 1501, a mirror 1601, a slit 2101 as a second slit, a slit 2201 as a third slit, a slit 2301 as a fourth slit, a slit 2401 as a fifth slit, a sensor 2501 as a first sensor, a sensor 2601 as a second sensor, a sensor 2701 as a third sensor, a sensor 2801 as the fourth sensor, a sensor 2901 as a fifth sensor, and a sensor 3001 as a sixth sensor. The optical path of the illumination light and the optical path of the light reflected by the sample 901 are shared from the sample 901 to the half mirror 701.

The sample 901 is placed on a stage 3101 that is movable in an X direction, a Y direction, and a Z direction. The sample 901 is, for example, a mask used to transfer a fine circuit pattern on a wafer or a glass substrate, a master pattern or a daughter pattern used in a nanoimprint lithography technology, or the like, but is not limited thereto. The sample 901 can be a wafer or a glass substrate where a pattern on a mask is transferred.

The light source 101 can be a laser light source. The wavelength of the light emitted from the light source 101 is set to 200 nm.

The light emitted from the light source 101 propagates along an optical axis 3201. Then, after the light is transmitted through the lens 401 and becomes the parallel light, a part of the light is transmitted through the slit 501 and is incident on the lens 601. The lens 601 is an imaging lens that refracts the incident light and condenses the light, and images the image of the light source 101. That is, the lens 601 images the image of the light source 101 at the position of the pupil of the objective lens 801.

Figure 6:
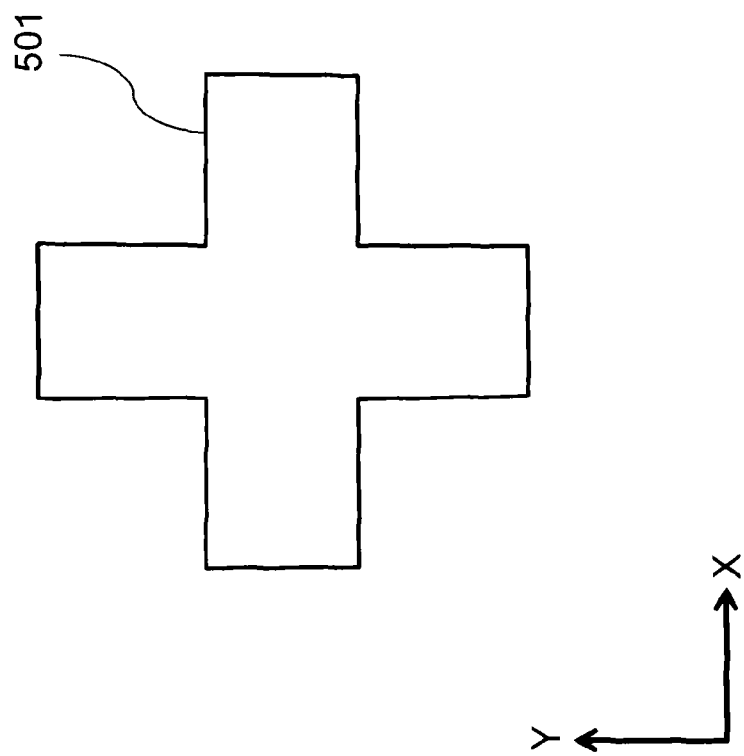
FIG. 6 is a plane view of a slit disposed in an illumination optical system according to the embodiment 2.

As illustrated in FIG. 6, the slit 501 has a cross shape in which two openings intersecting in the X direction and the Y direction are combined with each other. Further, a width of the opening is as thin as possible in order to approximate a line light source. Specifically, the width of the opening is preferably 1 μm or less.

The light refracted by the lens 601 is incident on the half mirror 701. The half mirror 701, for example, is disposed to be inclined 45 degrees with respect to the optical axis 3201. The half mirror 701 reflects about half of the incident light and transmits the remaining half. Therefore, a part of the light incident on the half mirror 701 from the lens 601 is reflected in a direction of the sample 901. That is, the optical axis 3201 is bent 90 degrees by the half mirror 701.

The illumination light reflected by the half mirror 701 is incident on the objective lens 801. The objective lens 801 can be configured such that a plurality of lenses is disposed in a lens barrel. The pupil of the objective lens 801 images an image of the light source 101. The objective lens 801 diffracts the incident light and then illuminates the sample 901. As described above, a part of the illumination light is transmitted through the slit 501. Therefore, the image of the slit 501 is projected on the sample 901. At this time, the image of the slit 501 is projected on a region different from an inspection field of view.

A part of the light transmitted through the lens 1001 is reflected by the mirror 1601 to bend the optical path and is incident on the lens 1301. Here, the reflection by the mirror 1601 makes the reflected light of the image of the slit 501 projected on the sample 901. The lens 1301 refracts the incident light and makes the refracted light incident on the half mirror 1701. The light reflected by the half mirror 1701 is incident on the sensor 2601.

The light, which is reflected by the mirror 1601, incident on the half mirror 1701 by the lens 1301, and transmitted through the half mirror 1701, is branched by the half mirror 1801.

The light transmitted through the half mirror 1801 incident on the half mirror 2001 by the lens 1501, and is further branched by the half mirror 2001. The light transmitted through the half mirror 1801 is transmitted through the slit 2301 and is then incident on the sensor 2901. On the other hand, the light reflected by the half mirror 2001 is transmitted through the slit 2401 and is then incident on the sensor 3001. Here, light transmitted through the slits 2301 and 2401 and incident on the sensors 2901 and 3001 is reflected light of the image of the slit 501 projected on the sample 901.

The slit 2301 is disposed in front of the focal position of the objective lens 801 (front focus), and the slit 2401 is disposed in the rear of the focal position of the objective lens 801 (rear focus). Further, the slit 2401 may be disposed in front of the focal position of the objective lens 801 (front focus), and the slit 2301 may be disposed in the rear of the focal position of the objective lens 801 (rear focus). The width of the slits 2301 and 2401 is a value corresponding to half the light beam spread by the numerical aperture NA of the objective lens 801, that is, half the pupil diameter of the objective lens 801. In the sensors 2901 and 3001, for example, a photodiode or a photomultiplier tube is preferably used.

The light, which is reflected by the half mirror 1801 is incident on the half mirror 1901 by the lens 1401. Here the light is further branched by the half mirror 1901. The light transmitted through the half mirror 1901 is transmitted through the slit 2101 and is then incident on the sensor 2701. On the other hand, the light reflected by the half mirror 1901 is transmitted through the slit 2201 and is then incident on the sensor 2801. Here, light transmitted through the slits 2101 and 2201 and incident on the sensors 2701 and 2801 is reflected light of the image of the slit 501 projected on the sample 901.

The slit 2101 is disposed in front of the focal position of the objective lens 801 (front focus), and the slit 2201 is disposed in the rear of the focal position of the objective lens 801 (rear focus). Further, the slit 2201 may be disposed in front of the focal position of the objective lens 801 (front focus), and the slit 2101 may be disposed in the rear of the focal position of the objective lens 801 (rear focus). The width of the slits 2101 and 2201 is a value corresponding to half the light beam spread by the numerical aperture NA of the objective lens 801, that is, half the pupil diameter of the objective lens 801. In the sensors 2701 and 2801, for example, a photodiode or a photomultiplier tube is preferably used.

The sensor 2601 is used to observe the light intensity distribution of the pupil of the illumination optical system (a'). When the light intensity distribution observed by the sensor 2601 is given as illustrated in FIG. 3, the influence of the diffracted light due to the change in the focal position becomes a problem. Here, in the example of FIG. 3, the diffracted light is generated in the X direction. That is, when the inspection target is a line-and-space pattern, the pattern is considered as a pattern elongated in the Y direction. In order not to be influenced by the diffracted light when adjusting the focal position, the direction in which the pattern is formed is not matched with the longitudinal direction of the slit-shaped illumination region. Therefore, in this case, the longitudinal direction of the slit-shaped illumination region is positioned in the X direction. On the other hand, in a case where the diffracted light is generated in the Y direction, the longitudinal direction of the slit-shaped illumination region is positioned in the Y direction.

Figure 8:
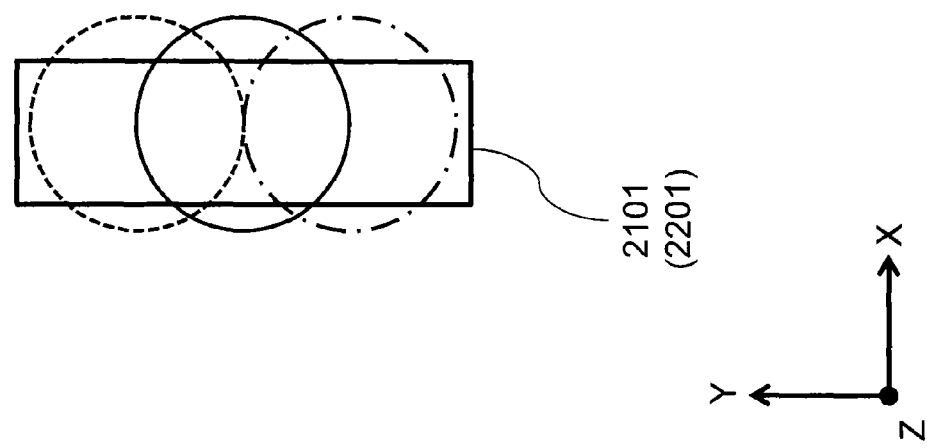
FIG. 8 is another plane view of a slit disposed in an imaging optical system according to the embodiment 2.
Figure 7:
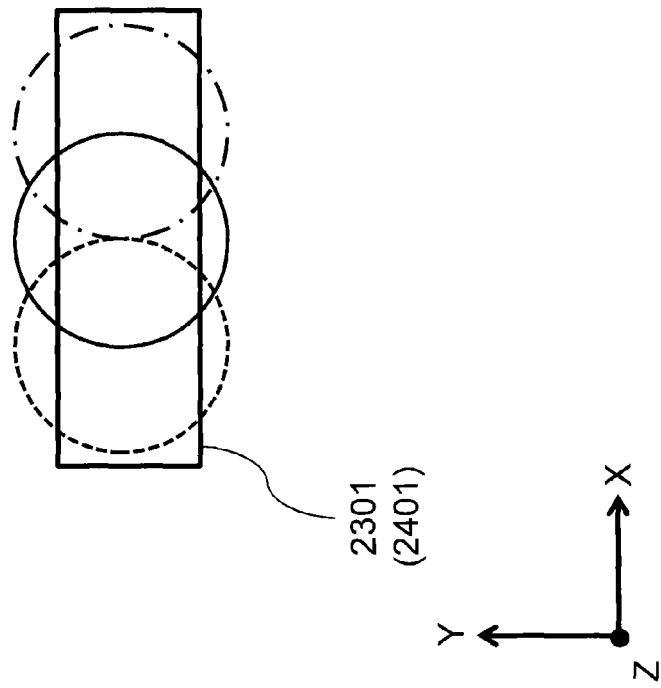
FIG. 7 is a plane view of a slit disposed in an imaging optical system according to the embodiment 2.

FIG. 7 is a plan view of the slits 2301 and 2401 of FIG. 5. On the other hand, FIG. 8 is a plan view of the slits 2101 and 2201 of FIG. 5. Further, the optical axis of the reflected light of the image of the slit 501 projected on the sample 901 is matched with the Z direction of FIGS. 7 and 8.

As illustrated in FIG. 7, the longitudinal directions of the slits 2301 and 2401 are the X direction. Therefore, as in the example of FIG. 3, in a case where the diffracted light is generated in the X direction, the influence of the diffracted light can be reduced by adjusting the focal position in a way of making the light transmitted through the slits 2301 and 2401 incident on the sensors 2901 and 3001.

On the contrary, as illustrated in FIG. 8, if the longitudinal directions of the slits 2101 and 2201 are the Y direction, it is effective in a case where the diffracted light is generated in the Y direction. That is, in this case, the influence of the diffracted light can be reduced by adjusting the focal position of the illumination optical system (a) in a way of making the light transmitted through the slits 2101 and 2201 incident on the sensors 2701 and 2801.

The sensor 2901 detects the light quantity of the front focus. On the other hand, the sensor 3001 detects the light quantity of the rear focus. When comparing the light quantity of the sensor 2901 with the light quantity of the sensor 3001 by changing the focal position of the light, a light quantity ratio of the sensor 2901 to the sensor 3001 is changed according to the shift amount of the focal position. A location where the light quantity ratio is 1:1 is the optimum focal position and has the maximum contrast.

The sensor 2701 detects the light quantity of the front focus. On the other hand, the sensor 2801 detects the light quantity of the rear focus. When comparing the light quantity of the sensor 2701 with the light quantity of the sensor 2801 by changing the focal position of the light, a light quantity ratio of the sensor 2701 to the sensor 2801 is changed according to the shift amount of the focal position. A location where a light quantity ratio is 1:1 is the optimum focal position and has the maximum contrast.

As mentioned in embodiment 1, when the output of the sensor being the front focus is α, the output of the sensor being the rear focus is β, and the output of the sensor without slit is γ, the displacement amount Z from the in-focus position of the object is given by Formula (4).

$$Z = f\left(\frac{\alpha}{\gamma}, \frac{\beta}{\gamma}\right) \tag{4}$$

A height of the stage 3101 is adjusted based on the displacement amount Z obtained using Formula (4), that is, the displacement amount from the in-focus position of the sample 901. Thereby, the focal position of the illumination light emitted from the light source 101 can be adjusted to be located on the pattern surface of the sample 901. Then, the optical image of the sample 901 is captured by the sensor 2501 and the defect inspection is performed using the acquired optical image.

Further, the optical path of the light imaged on the sensor 2501 is as follows. The light, which is emitted from the light source 101, transmitted through the lenses 401 and 601, and then reflected by the half mirror 701, is illuminated by the objective lens 801 on a region in which the pattern of the sample 901 to be inspected is provided. Further, the illumination light is not superimposed on the sample 901 with the image of the slit 501 projected on the sample 901. After that, the light reflected by the sample 901 propagates to the half mirror 701 along the optical path shared with the illumination light. Then, after the light transmitted through the half mirror 701 is transmitted through the lens 1001, the light is further transmitted through the lenses 1101 and 1201 and is imaged on the sensor 2501. Examples of the sensor 2501 include a line sensor in which CCD (charge coupled device) cameras being imaging elements are arranged in a row. In the line sensor, for example, a TDI (Time Delay Integration) sensor can be used.

According to the present embodiment, the reduction in the focal position adjustment accuracy due to the diffracted light can be prevented, making it possible to adjust the focal position.

Embodiment 3

The inspection method by die-to-database comparison method will be described in the present embodiment. Therefore, a reference image data which is compared with an optical image data of the sample to be inspected is a reference image data which is generated based on a design pattern data. Furthermore, as in an inspection of a template in a nanoimprint lithography (NIL), there may be a method for comparing a pixel focusing on a single image with an adjacent pixel thereto.

Figure 9:
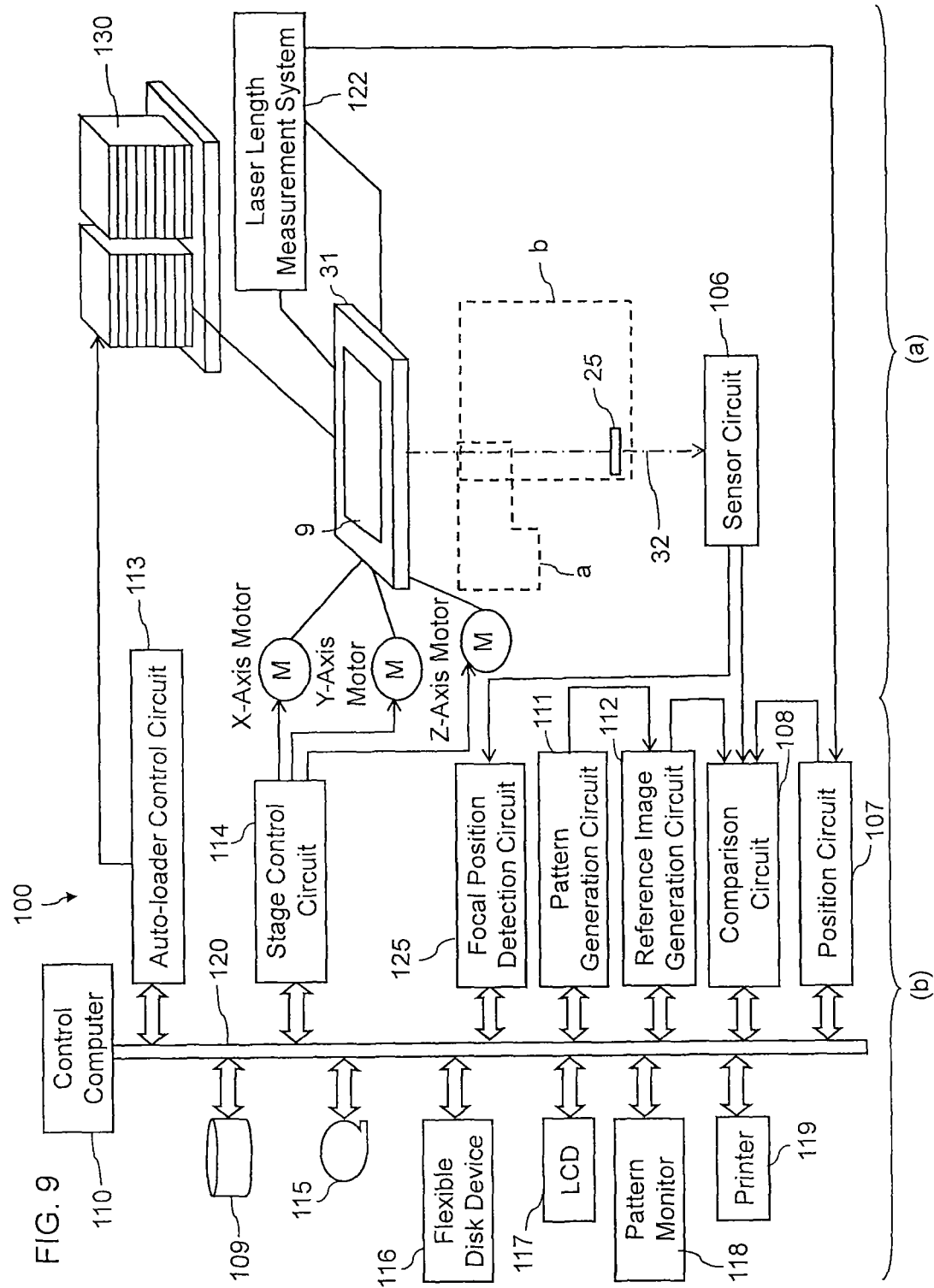
FIG. 9 is a schematic configuration diagram of an inspection apparatus according to the embodiment 3.

FIG. 9 is a schematic configuration diagram of an inspection apparatus according to the present embodiment. Portions (a) and (b) surrounded by dashed lines in FIG. 9 correspond to the illumination optical system (a) and the imaging optical system (b) of FIG. 4, respectively. In FIG. 9, portions other than the sensor 25 of FIG. 4 are omitted. Further, instead of the illumination optical system (a) and the imaging optical system (b) of FIG. 4, the illumination optical system (a') and the imaging optical system (b') of FIG. 5 may be applied to the inspection apparatus of FIG. 9.

In FIG. 9, a configuration unit necessary in the present embodiment is illustrated. However, another well-known configuration unit necessary for an inspection may be used. As used herein, a "unit" or "circuit" can be configured by a program operating on a computer. Alternatively, the "unit" or "circuit" may be constructed by not only the program that is software, but also a combination of software, hardware, or firmware. In the case that the "unit" or "circuit" may be constructed by the program, the program can be recorded in a recording device such as a magnetic disk drive.

As illustrated in FIG. 9, an inspection apparatus 100 includes a configuration unit A that constitutes an optical image acquisition circuit and a configuration unit B that performs processing necessary for an inspection using an optical image acquired by the configuration unit A.

As shown in FIG. 4, and described in embodiment 1, the optical system, that is, the configuration unit A is used for the focal position adjustment. The configuration unit A includes the illumination optical system (a) that illuminates the sample 9 in which the pattern to be inspected is formed, and the imaging optical system (b) that images the image of the pattern of the illuminated sample 9 on the light receiving surface of the sensor 25.

Further, the configuration unit A includes a stage 31 that is movable in the X direction, the Y direction, and the Z direction, a sensor circuit 106, a laser length measurement system 122, and an auto-loader 130. The stage 31, on which the sample 9 is placed, includes an XY stage that is movable in a horizontal direction (X direction and Y direction), and a Z stage that is placed on the XY stage and is movable in a vertical direction (Z direction). Furthermore, the XY stage can be configured to be movable in a rotating direction (θ direction).

The sample 9 is, for example, a mask used to transfer a fine circuit pattern on a wafer or a glass substrate, a master pattern or a daughter pattern used in a nanoimprint lithography technology, or the like, but is not limited thereto. The sample 9 can be a wafer or a glass substrate where a pattern on a mask is transferred.

In the configuration unit A, the optical image of a sample 9, that is, mask acquisition data is acquired. The mask acquisition data is an image of a mask in which a graphic pattern is written based on graphic data included in design pattern data of the sample 9. For example, the mask acquisition data is 8-bit data with no code, and expresses a gradation of brightness of each pixel.

The auto-loader 130 locates the sample 9 on the stage 31. An auto-loader control circuit 113 drives the auto-loader 130 under the control of a control computer 110. When the sample 9 is positioned on the stage 31, the patterns formed on the sample 9 are irradiated with light from the imaging optical system A light disposed under the stage 31. The light reflected on the sample 9 forms the optical image on the sensor 25 through the imaging optical system (b).

In order to obtain the optical image suitable for inspection, it is important to adjust the focus by accurately detecting the focal position of the light irradiated on the sample 9. As described in embodiment 1, the inspection apparatus 100 includes the illumination optical system (a) and the imaging optical system (b) and can prevent the reduction in the focal position adjustment accuracy due to the diffracted light and perform adjustment such that the focal position of the illumination light is located on the pattern surface of the sample 9.

Further, the inspection apparatus 100 may be configured to irradiate the light from above the sample 9 and guide the transmitted light to the sensor 25. By combining this configuration with the configuration illustrated in FIG. 9, each optical image can be simultaneously obtained by the transmitted light and the reflected light.

After the image of the pattern of the sample 9 is formed on the sensor 25, the sensor circuit 106 performs A/D (analog-digital) conversion to the image. A TDI (Time Delay Integration) sensor can be cited as an example of the sensor 25.

In the configuration unit B of the inspection apparatus 100, the control computer 110, that is, the controller controlling the whole of the inspection apparatus 100 is connected to a position circuit 107, a comparison circuit 108 as one example of a comparator, a reference image generation circuit 112 as one example of the reference image producing unit, an pattern generation circuit 111, a focal position detection circuit 125 as one example of the focal position detector, an auto-loader control circuit 113, a stage control circuit 114, a magnetic disk drive 109 as one example of storage, a network interface 115, a flexible disk device 116, a LCD 117, a pattern monitor 118, and a printer 119 through a bus 120 that constitutes a data transmission line. The stage 31 is driven by an X-axis motor, a Y-axis motor, and a Z-axis motor under the control of the stage control circuit 114. For example, an air slider, a linear motor, and a step motor can be used as these driving mechanisms and can further be used in any combination with each other.

As described above, the "unit" or "circuit" in FIG. 8 can be configured as a program operating on the computer. Alternatively, the "unit" or "circuit" may be constructed by not only the program, that is software, but also a combination of software and hardware, or software and firmware. In the case that the "unit" or "circuit" may be constructed by the program, the program can be recorded in the magnetic disk drive 109. For example, the sensor circuit 106, the auto-loader control circuit 113, the stage control circuit 114, the focal position detection circuit 125, pattern generation circuit 111, reference image generation circuit 112, the comparison circuit 108, and the position circuit 107 may be constructed by an electric circuit, the software that can be processed by the control computer 110, or the combination of the electric circuit and the software.

The focal position detection circuit 125 receives information from the sensor circuit 106 and detects the focal position. Specifically, the focal position of the illumination light is detected from the slit image (optical image of the slit 5 of FIG. 4) that is detected by the focal position detection sensors (27, 28, 29, and 30 of FIG. 4) disposed in the imaging optical system (b).

The control computer 110 controls the stage control circuit 114 based on the information from the focal position detection circuit 125 and moves the stage 31 in the Z direction such that the detected focal position is located on the pattern surface of the sample 9. In this manner, the focal position can accurately become the focal position.

The control computer 110 controls the stage control circuit 114 to drive the stage 31 along the x-axis and y-axis. A moving position of the stage 31 along the x-axis and y-axis is measured by the laser length measuring system 122, and transmitted to the position circuit 107.

The control computer 110 controls the auto-loader control circuit 113 to drive the auto-loader 130. The auto-loader 130 automatically conveys the sample 9, notifies an operator of an end of the inspection, reviews a defect as needed, and automatically discharges the sample 9.

The design pattern data that becomes reference image data of the die-to-database method is stored in the magnetic disk drive 109. In the progress of the inspection, the design pattern data is read and transmitted to the pattern generation circuit 111. The design pattern data will be described as follows.

CAD data produced by a designer (user) is converted into design intermediate data having a hierarchical format such as OASIS. The design pattern data, which is produced in each layer and formed on the mask, is stored in the design intermediate data. At this point, generally the inspection apparatus is configured not to directly read OASIS data. That is, independent format data is used by each manufacturer of an inspection apparatus. For this reason, the OASIS data is input to the inspection apparatus after conversion into format data unique to the inspection apparatus in each layer. In this case, the format data can be set to a data format that is unique to the inspection apparatus or to the data format that is compatible with a drawing apparatus used to draw patterns on a sample.

The format data is input to the magnetic disk drive 109 in FIG. 9. That is, the design pattern data used during the formation of the pattern on the sample 9 is stored in the magnetic disk drive 109.

In a graphic pattern included in the design pattern, a rectangle or a triangle is used as a basic graphic pattern. For example, Graphic data in which the shape, size, and position of each graphic pattern is stored in the magnetic disk drive 109. For example, the graphic data is information such as a coordinate (x, y) at a reference position of the graphic pattern, a side length, and a graphic code that becomes an identifier identifying a graphic pattern type such as a rectangle and a triangle.

A set of graphic patterns existing within a range of several hundreds of micrometers is generally called a cluster or a cell, and the data is layered using the cluster or cell. In the cluster or cell, a disposition coordinate and a repetitive amount are defined in the case that various graphic patterns are separately disposed or repetitively disposed with a certain distance. The cluster or cell data is disposed in a strip-shaped region called a stripe. The strip-shaped region has a width of several hundred micrometers and a length of about 100 mm that corresponds to a total length in an X-direction or a Y-direction of the sample 9.

As described above, the design pattern data is stored in the format data input to the magnetic disk drive 109. The design pattern data is read from the magnetic disk drive 109 through the control computer 110 by the pattern generation circuit 111.

In the pattern generation circuit 111, the design pattern data is converted into image data (bit pattern data). That is, the pattern generation circuit 111 expands the design pattern data to individual data of each graphic pattern, and interprets the graphic pattern code and graphic pattern dimension, which indicate the graphic pattern shape of the graphic pattern data. The design pattern data is expanded to binary or multi-level image data as the pattern disposed in a square having a unit of a grid of a predetermined quantization dimension. Then an occupancy rate of the graphic pattern in the design pattern is calculated in each region (square) corresponding to a sensor pixel, and the occupancy rate of the graphic pattern in each pixel becomes a pixel value.

The image data converted by the pattern generation circuit 111 is transmitted to the reference image generation circuit 112, that is, the reference image producing unit, and used to produce a reference image (also referred to as reference image data).

The optical image data output from the sensor circuit 106 is transmitted to the comparison circuit 108 together with data indicating a position of the sample 9 on the stage 31. The data is output from the position circuit 107. The reference image is also transmitted to the comparison circuit 108.

In the comparison circuit 108, the optical image data and the reference image data are compared to each other using a proper comparison determination algorithm. In the configuration of FIG. 9, reflection images are compared to each other. In a configuration in which a transmission optical system is used, transmission images are compared to each other, or a comparison determination algorithm in which transmission and reflection images are combined is used. As a result of the comparison, in the case that a difference between the two exceeds a predetermined threshold, the position is determined to be the defect.

The above-described strip is divided into sub-strips in an appropriate size. The data of the sub-strip extracted from the mask sampling data and the data of the sub-strip extracted from the reference image corresponding to the mask sampling data are input to the comparison unit of the comparison circuit 108. The input sub-strips are further divided into small rectangular regions called inspection frames and are compared in frame units by the comparison unit. In this way, the defect is detected. Several tens of comparison units are included in the comparison circuit 108 so as to concurrently process multiple inspection frames. Each comparison unit captures the unprocessed frame image when ending the processing of one inspection frame. Therefore, many inspection frames are sequentially processed.

An example of a method for inspecting the sample 9 with the inspection apparatus 100 in FIG. 9 will be described below.

<Focal Position Adjusting Process>

Further, as described in embodiment 1, the focal position is detected by irradiating the light from the light source provided in the illumination optical system (a) on the sample 9 and the detected position is adjusted to be the in-focus position.

Specifically, the projection pattern of the slit (slit 5 of FIG. 4) provided in the illumination optical system (a) is projected on the pattern surface of the sample 9, and the defocused image of the projected pattern, actually the light quantity, is detected by the sensors 29 and 30 or the sensors 27 and 28.

For example, the light from the light source (light source 1 of FIG. 4) emitting the light of the wavelength of 200 nm illuminates the sample 9 and the light intensity distribution of the pupil of the illumination optical system (a) is observed (by the sensor 26 of FIG. 4). As a result, in a case where the influence of the diffracted light due to the change in the focal position is not a problem, the focal position is adjusted using the light.

On the other hand, as a result of observing the light intensity distribution of the pupil of the illumination optical system (a) (by the sensor 26 of FIG. 4), the wavelength of the light illuminating the sample 9 is changed in a case where the amount of the diffracted light incident on the sensors (sensors 27, 28, 29, and 30 of FIG. 4) used to detect the focal position is changed by the focal position. That is, the focal position is detected by irradiating the light of the wavelength of 266 nm (from the light source 2 of FIG. 4).

Subsequently, the detected focal position is adjusted to be located on the pattern surface of the sample 9. Specifically, the focal position detection circuit 125 adjusts the Z-direction position of the stage 31 through the stage control circuit 114, such that the detected focal position is located on the pattern surface of the sample 9.

In the focal position detection circuit 125, the displacement amount Z from the in-focus position of the sample 9 is required by Formula (4) described in embodiment 1.

$$Z = f\left(\frac{\alpha}{\gamma}, \frac{\beta}{\gamma}\right) \quad (4)$$

The function f can be obtained by geometrically calculating blurring at each focal position with respect to the displacement amount Z and calculating a ratio of passing through the slit. Further, it can be obtained by an experiment using a test sample, a displacement amount of which is already known.

A height of the stage 31 is adjusted based on the displacement amount Z obtained using Formula (4). Specifically, the control computer 110 reads the displacement amount Z from the focal position detection circuit 125. Then, the stage control circuit 114 is controlled to shift the stage 31 in the Z direction, based on the displacement amount Z. In this way, the focal position can correctly become the in-focus position. According to this method, the reduction in the focal position adjustment accuracy due to the diffracted light can be prevented, making it possible to adjust the focal position.

<Optical Image Acquisition Process>

In the above manner, after the focal position is detected and the position of the sample 9 is adjusted such that the focal position is focused on the pattern surface of the sample 9, the optical image of the sample 9 is acquired in the configuration unit A of FIG. 9.

Figure 10:
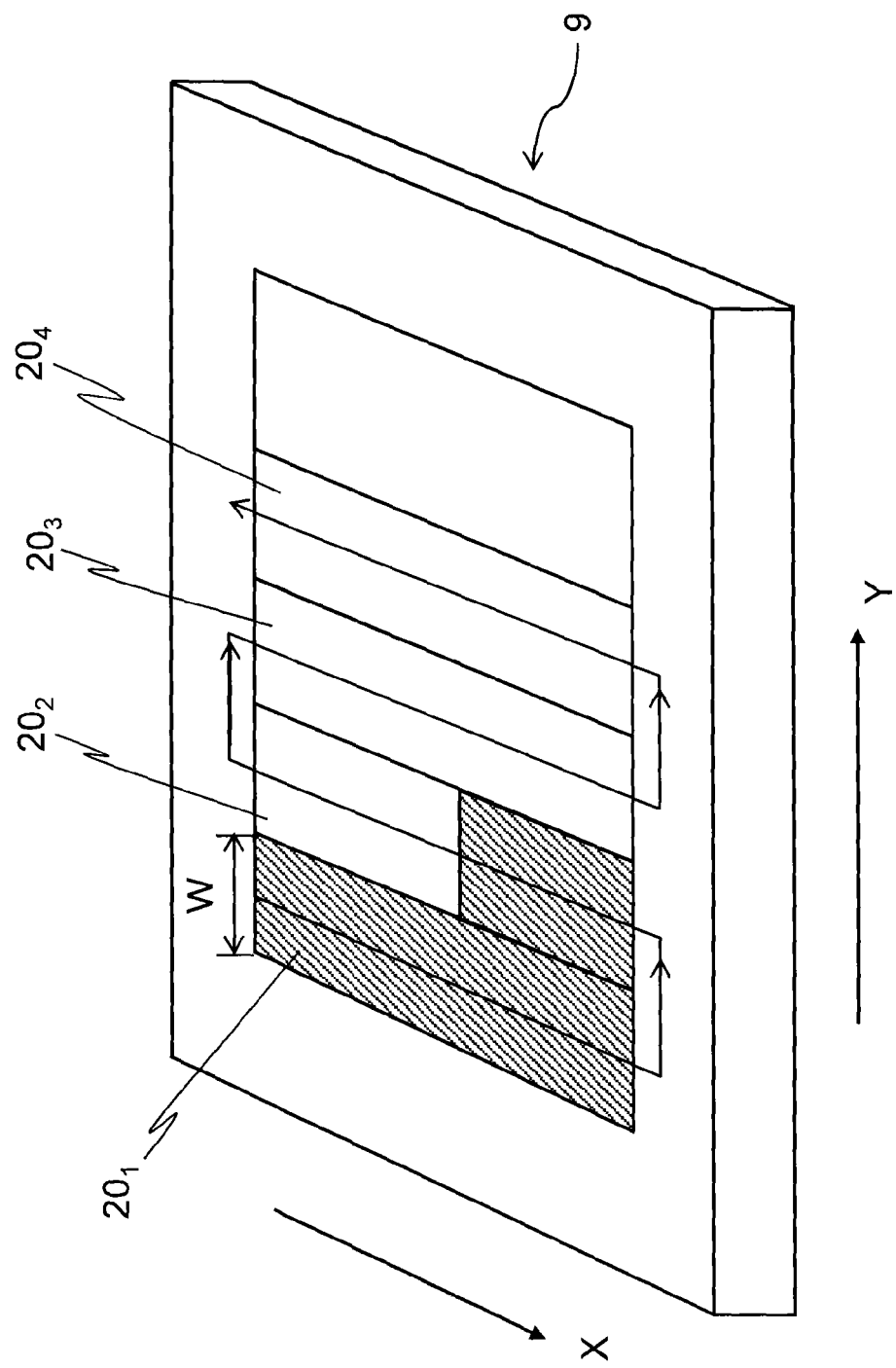
FIG. 10 is a view illustrating an optical image acquisition procedure for the pattern formed in the sample.

FIG. 10 is a view illustrating an optical image acquisition procedure for the pattern formed in the sample 9.

In FIG. 10, it is assumed that the sample 9 is positioned on the stage 31 in FIG. 9. The inspection region on the sample 9 is virtually divided into the strip-shaped multiple inspection regions, namely, stripes $20_1, 20_2, 20_3, 20_4, \ldots$ as illustrated in FIG. 10. For example, each stripe is a region having the width of several hundred micrometers and the length of about 100 mm corresponding to the total length in the X-direction or Y-direction of the sample 9.

The optical image is acquired in each stripe. That is, in acquiring the optical image in FIG. 10, the operation of the stage 31 is controlled such that the each stripe $20_1, 20_2, 20_3, 20_4, \ldots$ is continuously scanned. Specifically, the optical image on the sample 9 is acquired while the stage 31 moved in the −X-direction of FIG. 10. The image having a scan width W in FIG. 10 is continuously input to the sensor 25 in FIG. 9. That is, the image of the second stripe $20_2$ is acquired after the image of the first stripe $20_1$ is acquired. In this case, after the stage 31 moves in the −Y-direction in a stepwise manner, the optical image is acquired while the stage 31 moves in the direction (X-direction) opposite to the direction (−X-direction) in which the image of the first stripe $20_1$ is acquired, and the image having the scan width W is continuously input to the sensor 25. In the case that the image of the third stripe $20_3$ is acquired, after moving in the −Y-direction in the stepwise manner, the stage 31 moves in the direction opposite to the direction (X-direction) in which the image of the second stripe $20_2$ is acquired, namely, the direction (−X-direction) in which the image of the first stripe $20_1$ is acquired. An arrow in FIG. 10 indicates the optical image acquisition direction and sequence, and a hatched portion indicates the region where the optical image is already acquired.

The sensor circuit 106 performs the photoelectric conversion to the pattern image formed on the sensor 25 in FIG. 9, and the sensor circuit 106 performs the A/D (analog-digital) conversion to the pattern image. Then the optical image is transmitted from the sensor circuit 106 to the comparison circuit 108 in FIG. 9.

The A/D-converted sensor data is input to a digital amplifier (not illustrated) that can adjust an offset and a gain in each pixel. The gain for each pixel of the digital amplifier is fixed in a calibration process. For example, in the calibration process for transmitted light, a black level is fixed while the image of a light-shielding region on the sample 9, sufficiently wide with respect to an area in which the image is captured by the sensor, is captured. Then a white level is fixed while the image of a transmitted light region on the sample 9, sufficiently wide with respect to an area in which the image is captured by the sensor, is captured. At this point, in consideration of a fluctuation in light quantity during the inspection, the offset and the gain are adjusted in each pixel such that amplitudes of the white level and black level are distributed in a range of 10 to 240 corresponding to about 4% to about 94% of 8-bit gradation data.

<Reference Image Generating Process>

1. Storage Process

In the case of inspection by the die-to-database comparison method, the reference image generated from the design pattern data becomes a reference of the defect determination. In the inspection apparatus 100, the design pattern data used to form the pattern on the sample 9 is stored in the magnetic disk drive 109.

2. Pattern generating process

In the expansion process, the pattern generation circuit 111 in FIG. 9 reads the design pattern data from the magnetic disk drive 109 through the control computer 110, and converts the read design pattern data on the sample 9 into the binary or multi-value image data (design image data). The image data is transmitted to the reference image generation circuit 112.

3. Filtering Process

In the filtering process, the reference image generation circuit 112 in FIG. 9 performs the proper filtering to the design pattern data, that is, the graphic image data. The reason is as follows.

In the production process because roundness of the corner and a finished dimension of the line width is adjusted, the pattern on the sample 9 is not strictly matched with the design pattern. The optical image data, that is, the optical image obtained from the sensor circuit 106 in FIG. 9 is faint due to a resolution characteristic of the optical system or an aperture effect of the sensor 13, in other words, the state in which a spatial lowpass filter functions.

Therefore, the mask that becomes the inspection target is observed in advance of the inspection, a filter coefficient imitating the production process or a change of an optical system of the inspection apparatus is determined to subject the design pattern data to a two-dimensional digital filter. Thus, the processing of imitating the optical image is performed to the reference image.

The learning process of the filter coefficient may be performed using the pattern of the mask that becomes the reference fixed in the production process or a part of the pattern of the mask (in the present embodiment, sample 9) that becomes the inspection target. In the latter case, the filter coefficient is acquired in consideration of the pattern line width of the region used in the learning process or a finished degree of the roundness of the corner, and reflected in a defect determination criterion of the whole mask.

In the case that the mask that becomes the inspection target is used, advantageously the learning process of the filter coefficient can be performed without removing influences such as a variation of production lot and a fluctuation in condition of the inspection apparatus. However, when the dimension fluctuates in the surface of the mask, the filter coefficient becomes optimum with respect to the position used in the learning process, but the filter coefficient does not necessarily become optimum with respect to other positions, which results in a pseudo defect. Therefore, preferably the learning process is performed around the center of surface of the mask that is hardly influenced by the fluctuation in dimension. Alternatively, the learning process is performed at multiple positions in the surface of the mask, and the average value of the obtained multiple filter coefficients may be used.

<Die-to-Database Comparison Process>

The optical image data acquired in the optical image acquisition process is transmitted from the sensor circuit 106 to the comparison circuit 108. The reference image generation circuit 112 transmits the reference image data to the comparison circuit 108. The comparison circuit 108 compares the optical image data to the reference image data by the die-to-database method. Specifically, the captured image of the stripe data is extracted in units of inspection frames. Each of the inspection frames is compared to the data that becomes the reference of the defect determination using a proper comparison determination algorithm. The data that becomes the inspection target is determined to be the defect when the difference between the two exceeds the predetermined threshold. The information on the defect is stored as a mask inspection result. For example, the defect coordinate and the optical image and reference image, which are the basis of the defect determination are stored in the magnetic disk drive 109.

For example, it is assumed that a lattice-shaped chip pattern is formed in the sample 9. In the die-to-database comparison method, when the n-th chip is considered as the inspection target, the n-th chip is determined to be a defect in a case where the pattern difference between the optical image and the reference image of the n-th chip exceeds the predetermined threshold.

More specifically the defect determination can be made by the following two methods. One of the methods is the method for determining that the inspection target is the defect in the case that the difference exceeding a predetermined threshold is recognized between the position of a contour in the reference image and the position of a contour in the optical image. The other method is the method for determining that the inspection target is the defect in the case that the ratio of the pattern line width in the reference image and the pattern line width in the optical image exceeds a predetermined threshold. In this method, the ratio of the inter-pattern distance in the reference image and the inter-pattern distance in the optical image may be used.

<Review Process and Repairing Process>

The stored mask inspection result 205 is transmitted to a review tool. The review tool can be a component of the inspection apparatus or can be an external device of the inspection apparatus. A review process is an operation in which the operator determines whether the detected defect will become a practical problem. For example, the operator visually determines whether the defect needs to be corrected by comparing the reference image, that is the basis for the defect determination, to the optical image including the defect.

The defect information determined through the review process is also stored in the magnetic disk drive 109 of FIG. 9. When the defect to be corrected is confirmed by the review tool, the sample 9 is transmitted to a repair apparatus, that is, the external device of the inspection apparatus 100 together with a defect information list. Because a correction method depends on whether the defect is projected or recessed, a defect type including the distinction between the projection and the recess and the defect coordinate are added to the defect information list.

According to the above-described inspection method for the present embodiment, the reduction in the focal position adjustment accuracy due to the diffracted light can be prevented, making it possible to adjust the focal position. Therefore, the accurate inspection can be performed.

The present invention is not limited to the embodiments described and can be implemented in various ways without departing from the spirit of the invention.

The above description of the present embodiment has not specified apparatus constructions, control methods, etc. which are not essential to the description of the invention, since any suitable apparatus constructions, control methods, etc. can be employed to implement the invention. Further, the scope of this invention encompasses all focal position adjusting methods, inspection apparatuses, and inspection methods employing the elements of the invention and variations thereof, which can be designed by those skilled in the art.

What is claimed is:

1. A focal position adjusting method for an inspection apparatus, which includes an illumination optical system that illuminates at least one of light from a first light source and light from a second light source with a longer wavelength than the light from the first light source on a sample through an objective lens, and an imaging optical system that images light reflected by the sample on a first sensor through the objective lens, and performs a defect inspection of a pattern formed in the sample using the image imaged on the first sensor, the focal position adjusting method comprising:
    illuminating the light from the first light source on the sample through the objective lens after transmitting the light from the first light source through a first slit disposed in the illumination optical system;
    condensing the light from the first light source, which is reflected by the sample and transmitted through the objective lens, into a second sensor disposed in the imaging optical system, and observing a light intensity distribution of a pupil of the illumination optical system and from the light intensity distribution, in a case where most of diffracted light of the light from the first light source, which is reflected by the sample, is superimposed with $0^{th}$ order light, or in a case where it is determined that the diffracted light is not transmitted through two slits disposed in the imaging optical system branching the light from the first light source, which is reflected by the sample and transmitted through the objective lens, guiding the light to the two slits disposed in the imaging optical system, and adjusting a focal position of the illumination optical system by obtaining each light quantity of a front focus and a rear focus of an image of the first slit projected on the sample by a focal position adjustment sensor configured to detect light transmitted through one slit and another focal position adjustment sensor configured to detect light transmitted through the other slit, and from the light intensity distribution, in a case where it is determined that most of the diffracted light of the light from the first light source, which is reflected by the sample, is not superimposed with the $0^{th}$ order light and is transmitted through the two slits disposed in the imaging optical system, illuminating the light from the second light source on the sample through the objective lens after the light from the second light source is transmitted through the first slit by changing to the light from the first light source, branching the light reflected by the sample, guiding the light to the two slits disposed in the imaging optical system, and adjusting the focal position of the illumination optical system by obtaining each light quantity of the front focus and the rear focus of the image of the first slit projected on the sample by the focal position adjustment sensor configured to detect the light transmitted through one slit and the another focal position adjustment sensor configured to detect light transmitted through the other slit.

2. The focal position adjusting method according to claim 1, wherein the light from the first light source and the light from the second light source are illuminated on the sample, an optical path of the light from the first light source, which is reflected by the sample, and an optical path of the light from the second light source are separated by a light-separating unit provided in the imaging optical system, the two slits, through which the light from the first light source is transmitted, are the second slit and a third slit, the two slits, through which the light from the second light source is transmitted, are the fourth slit and a fifth slit, from the light intensity distribution, in a case where most of the diffracted light of the light from the first light source, which is reflected by the sample, is superimposed with $0^{th}$ order light, or in a case where it is determined that the diffracted light is not transmitted through the slits disposed in the imaging optical system, the focal position is adjusted by obtaining each light quantity of the front focus and the rear focus of the image of the first slit projected on the sample by a first focal position adjustment sensor configured to detect light transmitted through the second slit and a second focal position adjustment sensor configured to detect light transmitted through the third slit, and from the light intensity distribution, in a case where it is determined that most of the diffracted light of the light from the first light source, which is reflected by the sample, is not superimposed with the $0^{th}$ order light and is transmitted through the slits disposed in the imaging optical system, the focal position is adjusted by obtaining each light quantity of the front focus and the rear focus of the image of the first slit projected on the sample by a third focal position adjustment sensor configured to detect light transmitted through the fourth slit and a fourth focal position adjustment sensor configured to detect light transmitted through the fifth slit.

3. The focal position adjusting method according to claim 2, wherein the light-separating unit is a dichroic mirror.

4. A focal position adjusting method for an inspection apparatus, which includes an illumination optical system that illuminates light from a light source on a sample through an objective lens, and an imaging optical system that images light reflected by the sample on a first sensor through the objective lens, and performs a defect inspection of a pattern formed in the sample using the image imaged on the first sensor, the focal position adjusting method comprising:

illuminating the light from the light source on the sample through the objective lens after transmitting the light from the light source through a first slit;

branching the light from the light source, which is reflected by the sample and transmitted through the objective lens, condensing the light into a second sensor disposed in the imaging optical system, and observing a light intensity distribution of a pupil of the illumination optical system and in a case where it is determined from the light intensity distribution that diffracted light is generated in an X direction, further branching the branched light into at least two lights, guiding one of the branched lights to a second slit and a third slit, of which a longitudinal direction of an opening is an X direction, and adjusting the focal position by obtaining each light quantity of a front focus and a rear focus of an image of the first slit projected on the sample by a third sensor and a fourth sensor configured to detect light transmitted through the slits, respectively, and in a case where it is determined from the light intensity distribution that the diffracted light is generated in a Y direction, guiding the other light of the at least two branched lights to a fourth slit and a fifth slit, of which a longitudinal direction of an opening is a Y direction, and adjusting the focal position by obtaining each light quantity of the front focus and the rear focus of the image of the first slit projected on the sample by a fifth sensor and a sixth sensor configured to detect light transmitted through the slits, respectively.

5. The focal position adjusting method according to claim 4, wherein the first slit has a cross shape in which two openings intersecting in the X direction and the Y direction are combined with each other.

6. An inspection method, which uses an illumination optical system that illuminates at least one of light from a first light source and light from a second light source with a longer wavelength than the light from the first light source on a sample through an objective lens, and an imaging optical system that images light reflected by the sample on a first sensor through the objective lens, and performs a defect inspection of a pattern formed in the sample using the image imaged on the first sensor, the focal position adjusting method comprising:

illuminating the light from the first light source on the sample through the objective lens after transmitting the light from the first light source through a first slit disposed in the illumination optical system;

condensing the light from the first light source, which is reflected by the sample and transmitted through the objective lens, into a second sensor disposed in the imaging optical system, and observing a light intensity distribution of a pupil of the illumination optical system and from the light intensity distribution, in a case where most of diffracted light of the light from the first light source, which is reflected by the sample, is superimposed with $0^{th}$ order light, or in a case where it is determined that the diffracted light is not transmitted through two slits disposed in the imaging optical system branching the light from the first light source, which is reflected by the sample and transmitted through the objective lens, guiding the light to the two slits disposed in the imaging optical system, and adjusting a focal position of the illumination optical system by obtaining each light quantity of a front focus and a rear focus of an image of the first slit projected on the sample by a focal position adjustment sensor configured to detect light transmitted through one slit and another focal position adjustment sensor configured to detect light transmitted through the other slit, and from the light intensity distribution, in a case where it is determined that most of the diffracted light of the light from the first light source, which is reflected by the sample, is not superimposed with the $0^{th}$ order light and is transmitted through the two slits disposed in the imaging optical system, illuminating the light from the second light source on the sample through the objective lens after the light from the second light source is transmitted through the first slit by changing to the light from the first light source, branching the light reflected by the sample, guiding the light to the two slits disposed in the imaging optical system, and adjusting the focal position of the illumination optical system by obtaining each light quantity of the front focus and the rear focus of the image of the first slit projected on the sample by the focal position adjustment sensor configured to detect the light transmitted through one slit and the another focal position adjustment sensor configured to detect light transmitted through the other slit;

adjusting the position of the sample such that the focal position is focused on the pattern surface of the sample; and imaging light reflected by the sample on the first sensor through the objective lens and performing the defect inspection of the pattern of the sample using the image.

7. The inspection method according to claim 6, wherein the light from the first light source and the light from the second light source are illuminated on the sample, an optical path of the light from the first light source, which is reflected by the sample, and an optical path of the light from the second light source are separated by a light-separating unit provided in the imaging optical system, the two slits, through which the light from the first light source is transmitted, are the second slit and a third slit, the two slits, through which the light from the second light source is transmitted, are the fourth slit and a fifth slit, from the light intensity distribution, in a case where most of the diffracted light of the light from the first light source, which is reflected by the sample, is superimposed with $0^{th}$ order light, or in a case where it is determined that the diffracted light is not transmitted through the slits disposed in the imaging optical system, the focal position is adjusted by obtaining each light quantity of the front focus and the rear focus of the image of the first slit projected on the sample by a first focal position adjustment sensor configured to detect light transmitted through the second slit and a second focal position adjustment sensor configured to detect light transmitted through the third slit, and from the light intensity distribution, in a case where it is determined that most of the diffracted light of the light from the first light source, which is reflected by the sample, is not superimposed with the $0^{th}$ order light and is transmitted through the slits disposed in the imaging optical system, the focal position is adjusted by obtaining each light quantity of the front focus and the rear focus of the image of the first slit projected on the sample by a third focal position adjustment sensor configured to detect light transmitted through the fourth slit and a fourth focal position adjustment sensor configured to detect light transmitted through the fifth slit.

8. The inspection method according to claim 7, wherein the light-separating unit is a dichroic mirror.

9. An inspection method, which uses an illumination optical system that illuminates light from a light source on a sample through an objective lens, and an imaging optical system that images light reflected by the sample on a first sensor through the objective lens, and performs a defect inspection of a pattern formed in the sample using the image imaged on the first sensor, the focal position adjusting method comprising:

illuminating the light from the light source on the sample through the objective lens after transmitting the light from the light source through a first slit;

branching the light from the light source, which is reflected by the sample and transmitted through the objective lens, condensing the light into a second sensor disposed in the imaging optical system, and observing a light intensity distribution of a pupil of the illumination optical system and in a case where it is determined from the light intensity distribution that diffracted light is generated in an X direction, further branching the branched light into at least two lights, guiding one of the branched lights to a second slit and a third slit, of which a longitudinal direction of an opening is an X direction, and adjusting the focal position by obtaining each light quantity of a front focus and a rear focus of an image of the first slit projected on the sample by a third sensor and a fourth sensor configured to detect light transmitted through the slits, respectively, and in a case where it is determined from the light intensity distribution that the diffracted light is generated in a Y direction, guiding the other light of the at least two branched lights to a fourth slit and a fifth slit, of which a longitudinal direction of an opening is a Y direction, and adjusting the focal position by obtaining each light quantity of the front focus and the rear focus of the image of the first slit projected on the sample by a fifth sensor and a sixth sensor configured to detect light transmitted through the slits, respectively;

adjusting the position of the sample such that the focal position is focused on the pattern surface of the sample; and imaging light reflected by the sample on the first sensor through the objective lens and performing the defect inspection of the pattern of the sample using the image.

10. The inspection method according to claim 9, wherein the first slit has a cross shape in which two openings intersecting in the X direction and the Y direction are combined with each other.

\* \* \* \* \*